United States Patent
Zhang et al.

(10) Patent No.: US 7,417,030 B2
(45) Date of Patent: *Aug. 26, 2008

(54) INDAZOLE PEPTIDOMIMETICS AS THROMBIN RECEPTOR ANTAGONISTS

(75) Inventors: Han-Cheng Zhang, Lansdale, PA (US); Bruce E. Maryanoff, Forest Grove, PA (US); Anjali Pandey, Fremont, CA (US); Robert M. Scarborough, Half Moon Bay, CA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/393,529

(22) Filed: Mar. 30, 2006

(65) Prior Publication Data
US 2006/0166897 A1    Jul. 27, 2006

Related U.S. Application Data

(60) Continuation of application No. 10/403,218, filed on Mar. 31, 2003, now Pat. No. 7,049,297, which is a division of application No. 09/603,338, filed on Jun. 26, 2000, now abandoned.

(60) Provisional application No. 60/141,553, filed on Jun. 29, 1999.

(51) Int. Cl.
*A61K 38/00* (2006.01)
*A61K 31/416* (2006.01)
*C07K 5/00* (2006.01)
*C07D 277/04* (2006.01)

(52) U.S. Cl. ............... 514/19; 514/18; 514/385; 514/403; 530/330; 530/331; 548/146; 548/215; 548/305; 548/333.5

(58) Field of Classification Search ............... 514/18, 514/385, 403, 19; 530/330, 331; 548/146, 548/215, 305, 333.5
See application file for complete search history.

(56) References Cited

U.S. PATENT DOCUMENTS

| | | | | |
|---|---|---|---|---|
| 6,365,617 B1 * | 4/2002 | McComsey et al. | ...... | 514/403 |
| 6,630,451 B1 * | 10/2003 | Zhang et al. | ...... | 514/19 |
| 6,858,577 B1 * | 2/2005 | Zhang et al. | ...... | 514/2 |
| 7,049,297 B2 * | 5/2006 | Zhang et al. | ...... | 514/19 |

OTHER PUBLICATIONS

Cheseboro et al, "Antithrombotic Therapy and Progression of Coronary Artery Disease," CIRCULATION, 1992, pp. 100-110, vol. 86, No. 6[Supp III].
Verstraete et al, "Novel Antithrombotic Drugs in Development," DRUGS, 1995, pp. 856-884, vol. 49.
White, Harvey D., "Newer antiplatelet agents in acute coronary syndromes," J. Am Heart, 1999, pp. S570-S576, vol. 138.
Weksler, Babette B., "Antiplatelet Agents in Stroke Prevention," Cerebrovascular Diseases, 2000, pp. 41-48, vol. 10 (suppl 5).
Mousa et al, "Antiplatelet therapies: from aspirin to GPIIb/IIIa-receptor antagonists and beyond," Drug Discovery Today, 1999, pp. 552-561, vol. 4.
Andrade-Gordon et al, "Administration of a Potent Antagonist of Protease-Activated Receptor-1 (PAR-1) Attenuates Vascular Restenosis Following Balloon Angioplasty in Rats," J Pharmacol Exp Ther, 2001, pp. 34-42, vol. 298, No. 1, USA.
Derian et al, "Blockade of the Thrombin Receptor Protease-Activated Receptor-1 with a Small-Molecule Antagonist Prevents Thrombus Formation and Vascular Occlusion in Nonhuman Primates," J Pharmacol Exp., 2003, pp. 855-861, vol. 304, No. 2, USA.
Linde et al, "Pharmacological treatment for prevention of restenosis," Expert Opin Emerging Drugs, 2001, pp. 281-301, vol. 6, Ashley Publications.
Ischinger, Thomas, MD., "Antithrombotics in Interventional Cardiology; Optimizing Treatment and Strategies,", J Amer Cardiol, 1998, pp. 25L-28L, vol. 82, Excerpta Medica, Inc.
Schwartz, Robert S., "Pathophysiology of Restenosis: Interaction of Thrombosis, Hyperplasia, and/or Remodeling,", Am J Cardiol, 1998, pp. 14E-17E, vol. 81, Excerpta Medica, Inc.
Marx et al, "Rapamycin-FKBP Inhibits Cell Cycle Regulators of Proliferation in Vascular Smooth Muscle Cells,", Circ Res., 1995, pp. 412-417, vol. 76, American Heart Association, Inc.
Sollott et al, "Taxol Inhibits Neointimal Smooth Muscle Cell Accumulation after Angioplasty in the Rat,", The Journal of Clinical Invest., Inc., 1995, pp. 1869-1876, vol. 95.
Suzuki et al, "Stent-Based Delivery of Sirolimus Reduces Neointimal Formation in a Porcine Coronary Model," Circulation, 2001, pp. 1188-1193, vol. 104.

* cited by examiner

*Primary Examiner*—Jon Weber
*Assistant Examiner*—Abdel A Mohamed
(74) *Attorney, Agent, or Firm*—Yuriy Stercho

(57) ABSTRACT

The invention is directed to novel indazole peptidomimetic compounds which are useful as thrombin receptor antagonists for the treatment of diseases associated with thrombosis, restenosis, hypertension, heart failure, arrhythmia, inflammation, angina, stroke, atherosclerosis, ischemic conditions, Angiogenesis related disorders, cancer, and neurodegenerative disorders. Pharmaceutical compositions comprising the substituted indazole peptidomimetics of the present invention and methods of treating conditions mediated by the thrombin receptor are also disclosed.

18 Claims, No Drawings

SEQUENCE LISTING

```
<160> NUMBER OF SEQ ID NOS: 2

<210> SEQ ID NO 1
<211> LENGTH: 6
<212> TYPE: PRT
<213> ORGANISM: Homo sapiens

<400> SEQUENCE: 1

Ser Phe Leu Leu Arg Asn
1               5

<210> SEQ ID NO 2
<211> LENGTH: 7
<212> TYPE: PRT
<213> ORGANISM: Artificial Sequence
<220> FEATURE:
<223> OTHER INFORMATION: Sequence is an artificial peptide antagonist
      for PAR1 receptor.
<220> FEATURE:
<221> NAME/KEY: Unknown
<222> LOCATION: (2)
<223> OTHER INFORMATION: X is para-fluoro-phenylalanine
<220> FEATURE:
```

```
<221> NAME/KEY: Unknown
<222> LOCATION: (3)
<223> OTHER INFORMATION: X is homoarginine
<220> FEATURE:
<221> NAME/KEY: Unknown
<222> LOCATION: (5)
<223> OTHER INFORMATION: X is homoarginine

<400> SEQUENCE: 2

Ser Xaa Xaa Leu Xaa Lys Tyr
 1               5
```

INDAZOLE PEPTIDOMIMETICS AS THROMBIN RECEPTOR ANTAGONISTS

CROSS-REFERENCE TO RELATED APPLICATIONS

This patent application is a continuation of patent application Ser. No. 10/403,218, filed on Mar. 31, 2003, now U.S. Pat. No. 7, 049,297 issued on May 23, 2006, which is a division of patent application Ser. No. 09/603,338, filed on Jun. 26, 2000, now abandoned, which claims priority from provisional patent application Ser. No. 60/141,553, which was filed on Jun. 29, 1999. This invention relates to certain novel thrombin receptor antagonists, their synthesis and their use for the treatment of diseases associated with thrombosis, restenosis, hypertension, heart failure, arrhythmia, inflammation, angina, stroke, atherosclerosis, ischemic conditions, angiogenesis related disorders, cancer, and neurodegenerative disorders.

FIELD OF THE INVENTION

This invention relates to certain novel thrombin receptor antagonists, their synthesis and their use for the treatment of diseases associated with thrombosis, restenosis, hypertension, heart failure, arrhythmia, inflammation, angina, stroke, atherosclerosis, ischemic conditions, angiogenesis related disorders, cancer, and neurodegenerative disorders.

BACKGROUND OF THE INVENTION

Thrombin is an important serine protease in hemostasis and thrombosis. One of the key actions of thrombin is cellular modulation via receptor activation. A functional human thrombin receptor (PAR-1), cloned by Coughlin in 1991 (T.-K. Vu, *Cell* 1991, 64, 1057), was found to be a member of the G-protein coupled receptor (GPCR) superfamily. The receptor activation putatively occurs by N-terminal recognition and proteolytic cleavage at the Arg-41/Ser-42 peptide bond to reveal a truncated N-terminus. This new receptor sequence, which has an SFLLRN (Ser-Phe-Leu-Leu-Arg-Asn) (SEQ. ID. NO. 1) N-terminus acting as a tethered ligand to recognize a site on the receptor, can trigger activation and signal transduction leading to platelet aggregation. Since 1991, three other protease-activated receptors with extensive homology to the thrombin receptor, "PAR-2" (S. Nystedt, *Proc. Natl. Acad. Sci* USA 1994, 91, 9208), "PAR-3" (H. Ishihara, *Nature* 1997, 386, 502), and "PAR-4" (W.-F. Xu, *Proc. Natl. Acad. Sci* USA 1998, 95, 6642), have been cloned. Thrombin receptor (PAR-1) specific antibody-induced blockade of the platelet thrombin receptor has shown efficacy against arterial thrombosis in vivo (J. J. Cook *Circulation* 1995, 91, 2961). Hence, antagonists of the thrombin receptor (PAR-1) are useful to block these protease-activated receptors and, as such, may be used to treat platelet mediated thrombotic disorders such as myocardial infarction, stroke, restenosis, angina, atherosclerosis, and ischemic conditions.

The thrombin receptor (PAR-1) has also been identified on other cell types: endothelial, fibroblast, renal, osteosarcoma, smooth muscle, myocytes, tumor, and neuronal/glia. Thrombin activation of endothelial cells upregulates P-selectin to induce polymorphonuclear leukocyte adhesion—an inflammatory response of the vessel wall (Y. Sugama, J. Cell Biol. 1992, 119, 935). In fibroblasts, thrombin receptor (PAR-1) activation induces proliferation and transmission of mitogenic signals (D. T. Hung, *J. Cell Biol.* 1992, 116, 827). Thrombin has been implicated in osteoblast proliferation through its activation of osteoblast cells (D. N. Tatakis, *Biochem. Biophys. Res. Commun.* 1991, 174, 181). Thrombin has been implicated in the regulation and retraction of neurons (K. Jalink, *J. Cell. Biol.* 1992, 118, 411). Therefore, in this context, the antagonist compounds of this invention may also be useful against inflammation, osteoporosis, Angiogenesis related disorders, cancer, neurodegenerative disorders, hypertension, heart failure, arrhythmia, glomerulonephritis.

The compounds of the present invention are a structurally novel class of indazole peptidomimetics represented by the general formula (I) below.

SUMMARY OF THE INVENTION

The present invention is directed to structurally novel compounds represented by the following general formula (I):

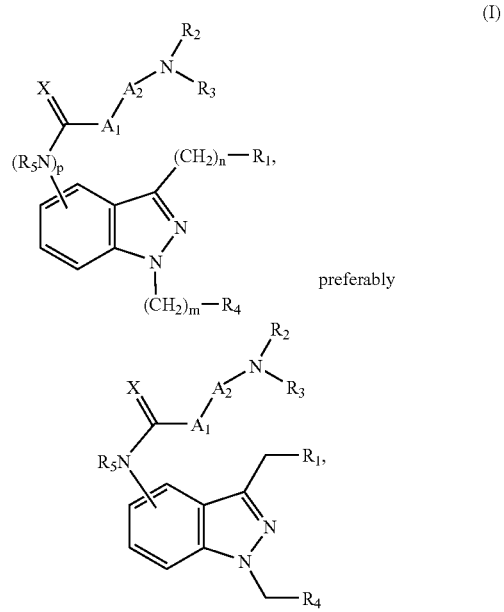

preferably wherein $A_1$ and $A_2$ are each independently a D- or L-amino acid selected from the group consisting of alanine, β-alanine, arginine, homoarginine, cyclohexylalanine, citrulline, cysteine (optionally substituted with $C_1$-$C_4$ alkyl, aryl, or ar$C_1$-$C_4$ alkyl), 2,4-diaminobutyric acid (optionally substituted with acyl, $C_1$-$C_4$ alkyl, aroyl, amidino, or MeC(NH)—), 2,3 diaminopropionic acid (optionally substituted with acyl, $C_1$-$C_4$ alkyl, aroyl, amidino, or MeC(NH)—), glutamine, glycine, indanylglycine, lysine (optionally substituted with acyl, $C_1$-$C_4$ alkyl, aroyl, MeC(NH)—), valine, methionine, proline, serine (optionally substituted with $C_1$-$C_4$ alkyl, aryl, or ar$C_1$-$C_4$ alkyl), homoserine (optionally substituted with $C_1$-$C_4$ alkyl, aryl, or ar$C_1$-$C_4$ alkyl), tetrahydroisoquinoline-3-COOH, threonine (optionally substituted with $C_1$-$C_4$ alkyl, aryl, or ar$C_1$-$C_4$ alkyl), ornithine (optionally substituted with acyl, $C_1$-$C_4$ alkyl, aroyl, MeC(NH)—), and an unsubstituted or substituted aromatic amino acid selected from the group consisting of phenylalanine, heteroarylalanine, naphthylalanine, homophenylalanine, histidine, tryptophan, tyrosine, arylglycine, heteroarylglycine, aryl-β-alanine, and heteroaryl-β-alanine wherein the substituents on the aromatic amino acid are independently selected from one or more of halogen, $C_1$-$C_4$ alkyl, $C_1$-$C_4$ alkoxy, hydroxy, $C_1$-$C_4$ alkoxycarbonyl, amino, amidino, guanidino, fluorinated $C_1$-$C_4$ alkyl, fluorinated $C_1$-$C_4$ alkoxy, $C_1$-$C_4$ alkylsulfonyl, $C_1$-$C_4$ alkylcarbonyl, cyano, aryl, heteroaryl, ar$C_1$-$C_4$ alkyl, $C_2$-$C_4$ alkenyl, alkynyl, or nitro;

$R_1$ is selected from amino, $C_1$-$C_8$ alkylamino, $C_1$-$C_8$ dialkylamino, arylamino, ar$C_1$-$C_8$ alkylamino, $C_3$-$C_8$ cycloalkylamino, heteroalkyl$C_1$-$C_8$ alkylamino, heteroalkyl$C_1$-$C_8$ alkyl-N-methylamino, $C_1$-$C_8$ dialkylamino$C_1$-$C_8$ alkylamino, —N($C_1$-$C_8$alkyl)-$C_1$-$C_8$ alkyl-N($C_1$-$C_8$alkyl)$_2$, N($C_1$-$C_8$alkyl)($C_1$-$C_8$alkenyl), —N($C_1$-$C_8$alkyl)($C_3$-$C_8$cycloalkyl), heteroalkyl or substituted heteroalkyl wherein the substituent on the heteroalkyl is selected from oxo, amino, $C_1$-$C_8$ alkoxy$C_1$-$C_8$ alkyl, $C_1$-$C_8$ alkylamino or $C_1$-$C_8$ dialkylamino;

Preferably, $R_1$ is selected from amino, $C_1$-$C_6$ alkylamino, $C_1$-$C_6$ dialkylamino, arylamino, ar$C_1$-$C_6$ alkylamino, heteroalkyl$C_1$-$C_6$ alkylamino, —N($C_1$-$C_6$alkyl)-$C_1$-$C_6$alkyl-N($C_1$-$C_6$alkyl)$_2$, heteroalkyl or substituted heteroalkyl wherein the substituent on the heteroalkyl is selected from oxo, amino, $C_1$-$C_6$ alkoxy$C_1$-$C_6$ alkyl, $C_1$-$C_6$ alkylamino or $C_1$-$C_6$ dialkylamino;

$R_2$ and $R_3$ are each independently selected from hydrogen, $C_1$-$C_8$ alkyl, $C_3$-$C_8$ cycloalkyl, $C_3$-$C_8$ cycloalkyl$C_1$-$C_8$ alkyl, aryl, heteroalkyl, substituted heteroalkyl (wherein the substituent on the heteroalkyl is one or more substituents independently selected from $C_1$-$C_8$ alkoxycarbonyl, $C_1$-$C_8$ alkyl, or $C_1$-$C_4$ alkylcarbonyl), heteroalkyl$C_1$-$C_8$ alkyl, indanyl, acetamidino$C_1$-$C_8$ alkyl, amino$C_1$-$C_8$ alkyl, $C_1$-$C_8$ alkylamino$C_1$-$C_8$ alkyl, $C_1$-$C_8$ dialkylamino$C_1$-$C_8$ alkyl, unsubstituted or substituted heteroaryl$C_1$-$C_8$ alkyl or unsubstituted or substituted ar$C_1$-$C_8$ alkyl, wherein the substituent on the aralkyl or heteroarylalkyl group is one or more substituents independently selected from halogen, nitro, amino, $C_1$-$C_8$ alkyl, $C_1$-$C_8$ alkoxy, hydroxy, cyano, $C_1$-$C_4$ alkylcarbonyl, $C_1$-$C_8$ alkoxycarbonyl, hydroxy$C_1$-$C_8$ alkyl or aminosulfonyl; or $R_2$ and $R_3$ together with the nitrogen to which they are attached, alternatively form an unsubstituted or substituted heteroalkyl group selected from piperidinyl, piperazinyl, morpholinyl or pyrrolidinyl, wherein the substituent is one or more substituents independently selected from $C_1$-$C_8$ alkyl $C_1$-$C_8$ alkoxycarbonyl or $C_1$-$C_4$ alkylcarbonyl;

Preferably, $R_2$ is selected from hydrogen or $C_1$-$C_6$ alkyl; and $R_3$ is selected from $C_1$-$C_8$ alkyl, $C_3$-$C_6$ cycloalkyl, $C_3$-$C_6$ cycloalkyl$C_1$-$C_6$ alkyl, aryl, heteroaryl$C_1$-$C_6$ alkyl, substituted heteroaryl$C_1$-$C_6$ alkyl wherein the substituent is $C_1$-$C_4$ alkyl, heteroalkyl, heteroalkyl$C_1$-$C_6$ alkyl, indanyl, acetamidino$C_1$-$C_6$ alkyl, amino$C_1$-$C_6$ alkyl, $C_1$-$C_6$ alkylamino$C_1$-$C_6$ alkyl, $C_1$-$C_6$ dialkylamino$C_1$-$C_6$ alkyl, ar$C_1$-$C_8$ alkyl, substituted ar$C_1$-$C_8$ alkyl wherein the substituent on the aralkyl group is one to five substituents independently selected from halogen, nitro, amino, $C_1$-$C_6$ alkyl, $C_1$-$C_6$ alkoxy, $C_1$-$C_6$ alkoxycarbonyl, hydroxyalkyl or aminosulfonyl; or $R_2$ and $R_3$, together with the nitrogen to which they are attached, alternatively form an unsubstituted or substituted heteroalkyl group selected from piperidinyl, piperazinyl or pyrrolidinyl, wherein the substituent is independently one or two substituents selected from $C_1$-$C_6$ alkyl;

$R_4$ is selected from unsubstituted or substituted aryl, ar$C_1$-$C_8$ alkyl, $C_3$-$C_8$ cycloalkyl, or heteroaryl, where the substituents on the aryl, ar$C_1$-$C_8$ alkyl, cycloalkyl or heteroaryl group are independently selected from one or more of halogen, nitro, amino, cyano, hydroxyalkyl, $C_1$-$C_8$ alkyl, $C_1$-$C_8$ alkoxy, hydroxy, $C_1$-$C_4$ alkylcarbonyl, $C_1$-$C_8$ alkoxycarbonyl, fluorinated $C_1$-$C_4$ alkyl, fluorinated $C_1$-$C_4$ alkoxy or $C_1$-$C_4$ alkylsulfonyl;

Preferably, $R_4$ is selected from unsubstituted or substituted aryl, ar$C_1$-$C_6$ alkyl, $C_3$-$C_6$ cycloalkyl or heteroaryl, where the substituents on the aryl, aralkyl, cycloalkyl or heteroaryl group are independently selected from one to three substituents selected from halogen, cyano, $C_1$-$C_4$ alkyl, $C_1$-$C_4$ alkoxy, $C_1$-$C_4$ alkoxycarbonyl, fluorinated $C_1$-$C_4$ alkyl, fluorinated $C_1$-$C_4$ alkoxy or $C_1$-$C_4$ alkylsulfonyl;

$R_5$ is selected from hydrogen or $C_1$-$C_8$ alkyl; preferably, $R_5$ is hydrogen X is oxygen or sulfur; preferably, X is oxygen;

m is an integer selected from 0, 1, 2 or 3;

n is an integer selected from 1 or 2;

p is an integer selected from 0 or 1; preferably, p is 1;

and pharmaceutically acceptable salts thereof.

In a preferred embodiment of the present invention:

$A_1$ is an L-amino acid selected from the group consisting of alanine, arginine, cyclohexylalanine, glycine, proline, tetrahydroisoquinoline-3-COOH, and an unsubstituted or substituted aromatic amino acid selected from the group consisting of phenylalanine, naphthylalanine, homophenylalanine, and O-methyl tyrosine, wherein the substituents on the aromatic amino acid are independently selected from one to five of (preferably, one to three of) halogen, $C_1$-$C_4$ alkyl, $C_1$-$C_4$ alkoxy, hydroxy, $C_1$-$C_4$ alkoxycarbonyl, amino, amidino, guanidino, fluorinated $C_1$-$C_4$ alkyl, fluorinated $C_1$-$C_4$ alkoxy, $C_1$-$C_4$ alkylsulfonyl, $C_1$-$C_4$ alkylcarbonyl, cyano, aryl, heteroaryl, ar$C_1$-$C_4$ alkyl, $C_2$-$C_4$ alkenyl, alkynyl, or nitro;

$A_2$ is an L-amino acid selected from the group consisting of alanine, β-alanine, arginine, citrulline, cysteine (optionally substituted with $C_1$-$C_4$ alkyl, aryl, or ar$C_1$-$C_4$ alkyl), 2,4-diaminobutyric acid (optionally substituted with acyl, $C_1$-$C_4$ alkyl, aroyl, amidino, or MeC(NH)—), 2,3-diaminopropionic acid (optionally substituted with acyl, $C_1$-$C_4$ alkyl, aroyl, amidino, or MeC(NH)—), glutamine, glycine, lysine (optionally substituted with acyl, $C_1$-$C_4$ alkyl, aroyl, MeC(NH)—), valine, methionine, serine (optionally substituted with $C_1$-$C_4$ alkyl, aryl, or ar$C_1$-$C_4$ alkyl), homoserine (optionally substituted with $C_1$-$C_4$ alkyl, aryl, or ar$C_1$-$C_4$ alkyl), threonine (optionally substituted with $C_1$-$C_4$ alkyl, aryl, or ar$C_1$-$C_4$ alkyl), ornithine (optionally substituted with acyl, $C_1$-$C_4$ alkyl, aroyl, MeC(NH)—), and an unsubstituted or substituted aromatic amino acid selected from the group consisting of phenylalanine, heteroarylalanine, and histidine, wherein the substituents on the aromatic amino acid are independently selected from one to five of (preferably, one to three of) halogen, $C_1$-$C_4$ alkyl, $C_1$-$C_4$ alkoxy, hydroxy, $C_1$-$C_4$ alkoxycarbonyl, amino, amidino, guanidino, fluorinated $C_1$-$C_4$ alkyl, fluorinated $C_1$-$C_4$ alkoxy, $C_1$-$C_4$ alkylsulfonyl, $C_1$-$C_4$ alkylcarbonyl, cyano, aryl, heteroaryl, ar$C_1$-$C_4$ alkyl, $C_2$-$C_4$ alkenyl, alkynyl, or nitro;

$R_2$ is selected from hydrogen or $C_1$-$C_4$ alkyl;

m and n are both 1;

and all other variables are as defined previously;

and pharmaceutically acceptable salts thereof.

In a class of the invention:

$A_1$ is an L-amino acid selected from the group consisting of alanine, arginine, cyclohexylalanine, glycine, proline, and an unsubstituted or substituted aromatic amino acid selected from the group consisting of phenylalanine, naphthylalanine, homophenylalanine, and O-methyl tyrosine, wherein the substituents on the aromatic amino acid are independently one to two substituents selected from halogen, $C_1$-$C_4$ alkyl, $C_1$-$C_4$ alkoxy, hydroxy, $C_1$-$C_4$ alkoxycarbonyl, amino, amidino, guanidino, fluorinated $C_1$-$C_4$ alkyl, fluorinated $C_1$-$C_4$ alkoxy, $C_1$-$C_4$ alkylsulfonyl, $C_1$-$C_4$ alkylcarbonyl, cyano, aryl, heteroaryl, ar$C_1$-$C_4$ alkyl, $C_2$-$C_4$ alkenyl, alkynyl, or nitro;

$A_2$ is an L-amino acid selected from the group consisting of alanine, □-alanine, arginine, citrulline, cysteine (optionally substituted with $C_1$-$C_4$ alkyl, aryl, or ar$C_1$-$C_4$ alkyl), 2,4-diaminobutyric acid (optionally substituted with acyl, $C_1$-$C_4$ alkyl, aroyl, amidino, or MeC(NH)—), 2,3-diaminopropionic acid (optionally substituted with acyl, $C_1$-$C_4$ alkyl, aroyl, amidino, or MeC(NH)—), glutamine, glycine, lysine (optionally substituted with acyl, $C_1$-$C_4$ alkyl, aroyl, MeC(NH)—), valine, methionine, serine (optionally substituted with $C_1$-$C_4$ alkyl, aryl, or ar$C_1$-$C_4$ alkyl), homoserine (optionally substituted with $C_1$-$C_4$ alkyl, aryl, or ar$C_1$-$C_4$ alkyl), threonine (optionally substituted with $C_1$-$C_4$ alkyl, aryl, or ar$C_1$-$C_4$ alkyl), ornithine (optionally substituted with acyl, $C_1$-$C_4$ alkyl, aroyl, MeC(NH)—), and an unsubstituted or substituted aromatic amino acid selected from the group consisting of phenylalanine, heteroarylalanine, and histidine, wherein the substituents on the aromatic amino acid are independently one to two substituents selected from halogen, $C_1$-$C_4$ alkyl, $C_1$-$C_4$ alkoxy, hydroxy, $C_1$-$C_4$ alkoxycarbonyl, amino, amidino, guanidino, fluorinated $C_1$-$C_4$ alkyl, fluorinated $C_1$-$C_4$ alkoxy, $C_1$-$C_4$ alkylsulfonyl, $C_1$-$C_4$ alkylcarbonyl, cyano, aryl, heteroaryl, ar$C_1$-$C_4$ alkyl, $C_2$-$C_4$ alkenyl, alkynyl, or nitro;

$R_1$ is selected from diethylamino, di-(n-propyl)amino,

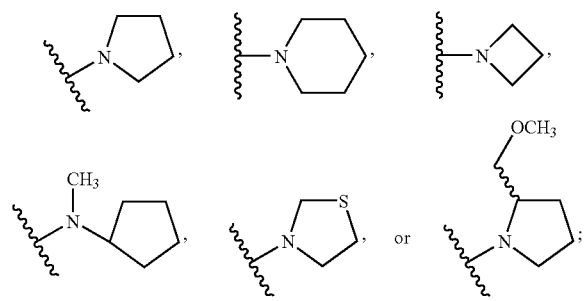

Preferably, $R_1$ is:

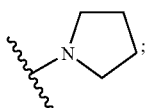

$R_2$ is selected from hydrogen, methyl or ethyl;

$R_3$ is selected from 2-indanyl, phenyl, cyclohexylmethyl, cyclopentyl, pyridylmethyl, furanylmethyl, 2-(4-methylfuranyl)methyl, thienylmethyl, diphenylmethyl, 4-imidazolylethyl, 2-(4-N-methyl)imidazolylethyl, n-octyl, phenyl-n-propyl, aminoethyl, aminopropyl, amino-n-pentyl, dimethylaminoethyl, 4-aminophenylsulfonylaminomethyl, acetamidineylethyl, 2-N-pyrrolidinylethyl, N-ethoxycarbonylpiperidinyl, unsubstituted or substituted phenylethyl or unsubstituted or substituted benzyl wherein the substituents on the phenylethyl or benzyl are independently one or two substituents selected from methyl, fluorine, chlorine, nitro, methoxy, methoxycarbonyl or hydroxymethyl; or $R_2$ and $R_3$, together with the nitrogen to which they are attached, form a heteroalkyl group selected from piperidinyl, or 4-(N-methyl)piperazinyl;

$R_4$ is selected from cyclohexyl, 2-naphthyl, phenylethyl, 4-fluorophenylethyl, or unsubstituted or substituted phenyl, where the substituents on the phenyl are independently selected from one to two substituents selected from fluorine, chlorine, iodine, methyl, cyano, or trifluoromethyl;

Preferably, $R_4$ is 2,6-dichlorophenyl or 2-methylphenyl;

all other variables are as defined previously;

and pharmaceutically acceptable salts thereof.

In a subclass of the invention, $A_1$ is selected from 3,4-Difluorophenylalanine or 4-Chlorophenylalanine;

$A_2$ is selected from 2,4-Diaminobutyric acid or 4-Pyridylalanine;

$R_2$ is hydrogen;

$R_3$ is selected from benzyl or 2-aminoethyl;

all other variables are as defined previously;

and pharmaceutically acceptable salts thereof.

Illustrative of the invention is a pharmaceutical composition comprising a pharmaceutically acceptable carrier and any of the compounds described above. Illustrating the invention is a pharmaceutical composition made by mixing any of the compounds described above and a pharmaceutically acceptable carrier. An illustration of the invention is a process for making a pharmaceutical composition comprising mixing any of the compounds described above and a pharmaceutically acceptable carrier.

An example of the invention is a method of treating a disorder (preferably, a platelet-mediated thrombotic disorder) selected from arterial and/or venous thrombosis, acute myocardial infarction, reocclusion following thrombolytic therapy and/or angioplasty, inflammation, unstable angina, stroke, restenosis, atherosclerosis, ischemic conditions, hypertension, heart failure, arrhythmia, glomerulonephritis, osteoporosis, Angiogenesis related disorders, cancer, neurodegenerative disorders and a variety of vaso-occlusive disorders in a subject in need thereof comprising administering to the subject a therapeutically effective amount of any of the compounds or pharmaceutical compositions described above. In a preferred embodiment, the therapeutically effective amount of the compound is from about 0.1 mg/kg/day to about 300 mg/kg/day.

Also included in the invention is the use of any of the compounds described above for the preparation of a medicament for a disorder (preferably, a platelet-mediated thrombotic disorder) selected from arterial and/or venous thrombosis, acute myocardial infarction, reocclusion following thrombolytic therapy and/or angioplasty, inflammation, unstable angina, stroke, restenosis, atherosclerosis, ischemic conditions, hypertension, heart failure, arrhythmia, glomerulonephritis, osteoporosis, Angiogenesis related disorders, cancer, neurodegenerative disorders or a variety of vaso-occlusive disorders in a subject in need thereof.

DETAILED DESCRIPTION OF THE INVENTION

More particularly, the present invention is directed to compounds of the following formula (I):

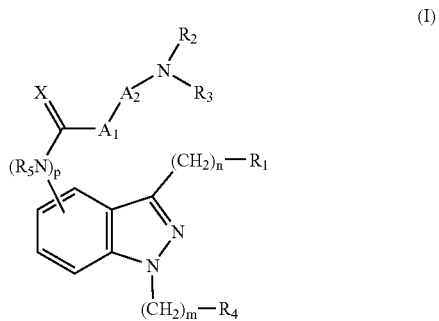

(I)

wherein $A_1$, $A_2$, $R_1$, $R_2$, $R_3$, $R_4$, $R_5$, X, m, n and p are as previously defined. In a particularly preferred embodiment, the compounds have the formula

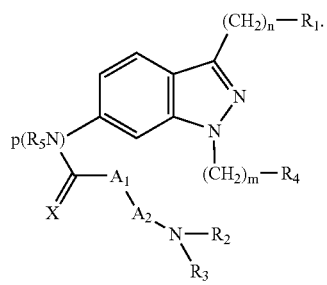

The compounds of the present invention are thrombin receptor antagonists and as such are useful in treating thrombosis, restenosis, hypertension, heart failure, arrhythmia, myocardial infarction, glomerulonephritis, reocclusion following thrombolytic therapy, reocclusion following angioplasty, inflammation, angina, stroke, atherosclerosis, ischemic conditions, a vaso-occlusive disorder, neurodegenerative disorders, Angiogenesis related disorders and cancer. These compounds are also useful as antithrombotics in conjunction with fibrinolytic therapy (e.g., t-PA or streptokinase).

In the compounds of formula (I), the amino acid residues comprising the $A_1$ and $A_2$ substituents are attached to the adjacent moiety according to standard nomenclature so that the amino-terminus (N-terminus) of the amino acid is drawn on the left and the carboxy-terminus of the amino acid is drawn on the right. So, for example, in Compound 1, where $A_1$ is 3,4-difluorophenylalanine and $A_2$ is Dbu (2,4-Diaminobutyric acid), the N-terminus of the 3,4-difluorophenylalanine ($A_1$) is attached to the carbonyl group and the carboxy-terminus of the 3,4-difluorophenylalanine ($A_1$) is attached to the N-terminus of the $A_2$ substituent (Dbu), similarly, the N-terminus of the Dbu ($A_2$) is attached to the carboxy-terminus of the $A_1$ substituent and the carboxy-terminus of the Dbu ($A_2$) is attached to the N—$R_2R_3$ group.

When a particular group is "substituted" (e.g., Phe, aryl, heteroalkyl, heteroaryl), that group may have one or more substituents, preferably from one to five substituents, more preferably from one to three substituents, most preferably from one to two substituents, independently selected from the list of substituents.

Under standard nomenclature used throughout this disclosure, the terminal portion of the designated side chain is described first, followed by the adjacent functionality toward the point of attachment. Thus, for example, a "phenyl$C_1$-$C_6$ alkylamido$C_1$-$C_6$alkyl" substituent refers to a group of the formula

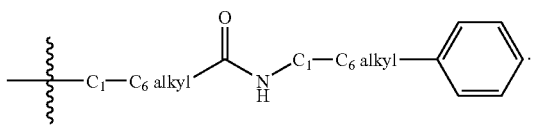

The compounds of the present invention may also be present in the form of a pharmaceutically acceptable salt. The pharmaceutically acceptable salt generally takes a form in which the basic nitrogen is protonated with an inorganic or organic acid. Representative organic or inorganic acids include hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, unless otherwise noted alkyl and alkoxy whether used alone or as part of a substituent group, include straight and branched chains having 1 to 8 carbon atoms, or any number within this range. For example, alkyl radicals include methyl, ethyl, propyl, isopropyl, n-butyl, isobutyl, sec-butyl, t-butyl, n-pentyl, 3-(2-methyl)butyl, 2-pentyl, 2-methylbutyl, neopentyl, n-hexyl, 2-hexyl and 2-methylpentyl. Alkoxy radicals are oxygen ethers formed from the previously described straight or branched chain alkyl groups. Cycloalkyl groups contain 3 to 8 ring carbons and preferably 5 to 7 carbons. Similarly, alkenyl and alkynyl groups include straight and branched chain alkenes and alkynes having 1 to 8 carbon atoms, or any number within this range.

The term "aryl" as used herein refers to an unsubstituted or substituted aromatic group such as phenyl and naphthyl. The term "aroyl" refers to the group —C(O)-aryl.

The term "heteroalkyl" as used herein represents an unsubstituted or substituted stable three to seven membered monocyclic saturated ring system which consists of carbon atoms and from one to three heteroatoms selected from N, O or S, and wherein the nitrogen or sulfur heteroatoms may optionally be oxidized, and the nitrogen heteroatom may optionally be quaternized. The heteroalkyl group may be attached at any heteroatom or carbon atom which results in the creation of a stable structure. Examples of such heteroalkyl groups include, but are not limited to azetidinyl, piperidinyl, pyrrolidinyl, piperazinyl, oxopiperazinyl, oxopiperidinyl, oxoazepinyl, azepinyl, tetrahydrofuranyl, dioxolanyl, tetrahydroimidazolyl, tetrahydrothiazolyl, tetrahydrooxazolyl, tetrahydropyranyl, morpholinyl, thiomorpholinyl, thiamorpholinyl sulfoxide, thiamorpholinyl sulfone and oxadiazolyl. Preferred heteroalkyl groups include pyrrolidinyl, piperidinyl, piperazinyl, morpholinyl, azetidinyl and tetrahydrothiazolyl.

The term "heteroaryl" as used herein represents an unsubstituted or substituted stable five or six membered monocyclic aromatic ring system or an unsubstituted or substituted nine or ten membered benzo-fused heteroaromatic ring system or bicyclic heteroaromatic ring system which consists of carbon atoms and from one to four heteroatoms selected from N, O or S, and wherein the nitrogen or sulfur heteroatoms may optionally be oxidized, and the nitrogen heteroatom may optionally be quaternized. The heteroaryl group may be attached at any heteroatom or carbon atom that results in the creation of a stable structure. Examples of heteroaryl groups include, but are not limited to pyridyl, pyridazinyl, thienyl, furanyl, imidazolyl, isoxazolyl, oxazolyl, pyrazolyl, pyrrolyl, thiazolyl, thiadiazolyl, triazolyl, benzimidazolyl, benzofuranyl, benzothienyl, benzisoxazolyl, benzoxazolyl, benzopyrazolyl, indolyl, benzothiazolyl, benzothiadiazolyl, benzotriazolyl adeninyl or quinolinyl. Prefered heteroaryl groups include pyridyl, pyrrolyl, pyrazinyl, thiadiazolyl, pyrazolyl, thienyl, triazolyl and quinolinyl.

The term "aralkyl" means an alkyl group substituted with one, two or three aryl groups (e.g., benzyl, phenylethyl, diphenylmethyl, triphenylmethyl). Similarly, the term "aralkoxy" indicates an alkoxy group substituted with an aryl group (e.g., benzyloxy). The term aminoalkyl refers to an alkyl group substituted with an amino group (i.e., -alkyl-$NH_2$). The term "alkylamino" refers to an amino group substituted with an alkyl group (i.e., —NH-alkyl). The term "dialkylamino" refers to an amino group which is disubstituted with alkyl groups wherein the alkyl groups can be the same or different (i.e., —N-[alkyl]$_2$).

The term "acyl" as used herein means an organic radical having 1 to 6 carbon atoms (branched or straight chain) derived from an organic acid by removal of the hydroxyl group.

The term "oxo" refers to the group =O.

The term "carbonyl" refers to the group C(O).

The term "halogen" shall include iodine, bromine, chlorine and fluorine.

Whenever the term "alkyl" or "aryl" or either of their prefix roots appear in a name of a substituent (e.g., aralkyl, dialkylamino) it shall be interpreted as including those limitations given above for "alkyl" and "aryl." Designated numbers of carbon atoms (e.g., $C_1$-$C_6$) shall refer independently to the number of carbon atoms in an alkyl or cycloalkyl moiety or to the alkyl portion of a larger substituent in which alkyl appears as its prefix root.

As used herein, the term "phosgene equivalent" represents the class of carbonic acid derivatives which include 4-nitrophenyl chloroformate, phosgene or "$COCl_2$," phenyl chloroformate, triphosgene or "$(CCl_3O)_2CO$," carbonyldiimidazole, diethyl carbonate or diphenyl carbonate.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

As used herein, the term "composition" is intended to encompass a product comprising the specified ingredients in the specified amounts, as well as any product which results, directly or indirectly, from combinations of the specified ingredients in the specified amounts. Accordingly, pharmaceutical compositions containing the compounds of the present invention as the active ingredient as well as methods of preparing the instant compounds are also part of the present invention.

Particularly preferred compounds of the present invention and their biological data are shown in Table 1, as follows; the amino acids bear the "L" absolute configuration unless denoted otherwise. Table 1 contains $IC_{50}$ values (μM) of the compounds in a thrombin receptor binding assay, and $IC_{50}$ values (μM) against platelet aggregation stimulated by thrombin.

TABLE 1

Indazole Peptidomimetics As Thrombin Receptor (PAR-1) Antagonists

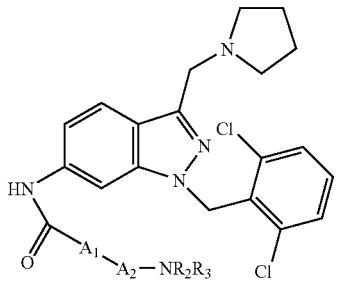

| Comp | A$_1$ | A$_2$ | R$_2$R$_3$N | Thr GFP Aggr[a] | Thr Recptr Bdg[b] |
|---|---|---|---|---|---|
| 1 | 3,4-DiF-Phe[c] | Dbu[d] | PhCH$_2$NH | 0.31 | 0.04 |
| 2 | 4-Cl—Phe | Dbu | PhCH$_2$NH | 0.26 | 20 |
| 3 | 3,4-DiF—Phe | 4-Pyrala[e] | H$_2$NCH$_2$CH$_2$NH | 0.50 | 0.03 |
| 4 | 3,4-DiF—Phe | Dbu | R—PhCH(Me)NH | 0.32 | 0.15 |
| 5 | 3,4-DiF—Phe | Dbu | S—PhCH(CH$_2$OH)NH | 0.66 | 0.32 |
| 6 | 4-Cl—Phe | 2-Thiala[f] | H$_2$NCH$_2$CH$_2$NH | 0.30 | 5.8 |

[a]Thrombin-induced gel-filtered platelet aggregation assay.
[b]Thrombin receptor (PAR-1) binding assay.
[c]3,4-Difluorophenylalanine.
[d]2,4-Diaminobutyric acid.
[e]4-Pyridylalanine.
[f]2-Thienylalanine.

The antagonists of the present invention may be prepared via a convergent solution-phase synthesis by coupling an aminoindazole intermediate AAG4 with a dipeptide amine AAG6 via a urea linkage as described in the general Scheme AAGeneric. The appropriately nitro substituted indole AAG1 (Scheme AAGeneric) was treated with aqueous NaNO$_2$ under acidic conditions (pH from about pH 1 to about pH 2) to give (via nitrosation, G. Buchi, *J. Am. Chem. Soc.* 1986, 108, 4115) 3-indazolecarboxaldehyde AAG2. Reductive amination of AAG2 with an amine such as pyrrolidine and a reducing agent such as sodium triacetoxyborohydride afforded AAG3. Alkylation of AAG3 with a substituted aralkyl or heteroaryl alkyl halide and a base such as potassium hydroxide in an aprotic solvent such as THF to give an intermediate, which was reduced in a classical manner with, for example, iron and acetic acid or with a newer method such as dimethyl hydrazine and iron to give aminoindazole intermediate AAG4.

Dipeptide amine AAG6 can be synthesized from the corresponding protected amino acids using standard peptide coupling conditions. Thus, an Fmoc protected amino-acid (A$_2$), AAG5 (Scheme AAGeneric), was coupled to amine R$_2$R$_3$NH using a coupling agent such as dicyclohexylcarbodiimide (DCC) or diisopropylcarbodiimide (DIC) and 1-hydroxybenzotriazole (HOBT) in a dipolar aprotic solvent like DMF to give the amide, which was Fmoc deprotected with a dialkylamine in a dipolar aprotic solvent such as diethylamine in acetonitrile. The resulting amine was coupled to the second Fmoc protected amino-acid (A$_1$) in the same way with a coupling agent such as DIC and HOBT in a dipolar aprotic solvent like DMF to give the dipeptide, which was Fmoc deprotected as above with a dialkylamine in a dipolar aprotic solvent like acetonitrile to afford dipeptide amine AAG6.

Aminoindazole intermediate AAG2 was then treated with a phosgene equivalent such as 4-nitrophenyl chloroformate or triphosgene and a base like diisopropylethylamine in a solvent such as dichloromethane, and to this was then added dipeptide amine AAG6 to give an urea. Removal of the protecting group, if necessary, such as Boc group with an acid such as trifluoroacetic acid from the side chain of dipeptide afforded final targets AAG7.

SCHEME AAGeneric

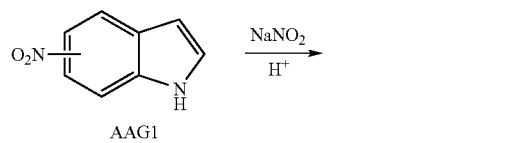

AAG1

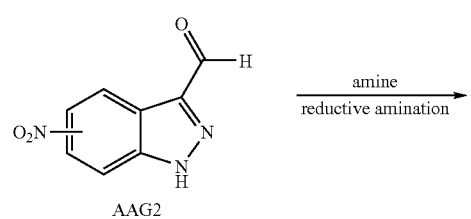

AAG2

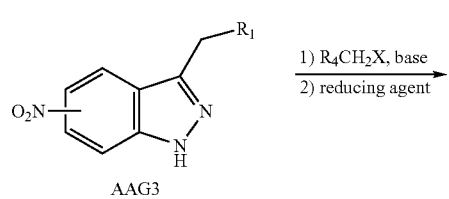

AAG3

-continued

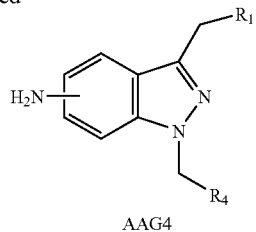

AAG4

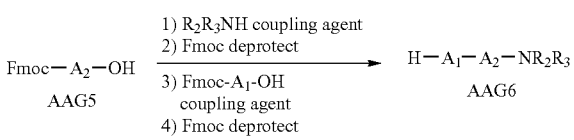

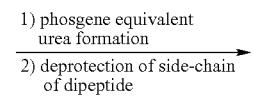

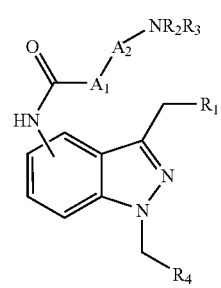

AAG7

As a typical example of this convergent solution-phase method, synthesis of compound 1 was presented in Scheme AA. Thus, treatment of 6-nitroindole AA1 with aqueous NaNO$_2$ under acidic condition (pH from about pH 1 to about pH 2) afforded 3-indazolecarboxaldehyde (AA2). Reductive amination of AA2 with pyrrolidine/NaB(OAc)$_3$H was followed by alkylation with 2,6-diCl-Bn-Br and nitro reduction with Me$_2$NNH$_2$/FeCl$_3$ to provide aminoindazole intermediate AA4. Coupling of N-☐-Fmoc-N-☐-Boc-diaminobutyric acid (AA5) with benzyl amine in the presence of DCC and HOBt was followed by de-protection of Fmoc group with diethylamine. The resulting intermediate was coupled with Fmoc-3,4-diF-Phe-OH using DIC/HOBt and treated with diethylamine to give dipeptide amine AA6. Urea formation between dipeptide amine AA6 and 6-aminoindazole AA4 in the presence of 4-nitrophenylchloroformate was followed by de-protection of Boc group with TFA to afford target compound 1.

SCHEME AA

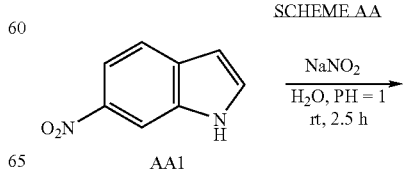

AA1

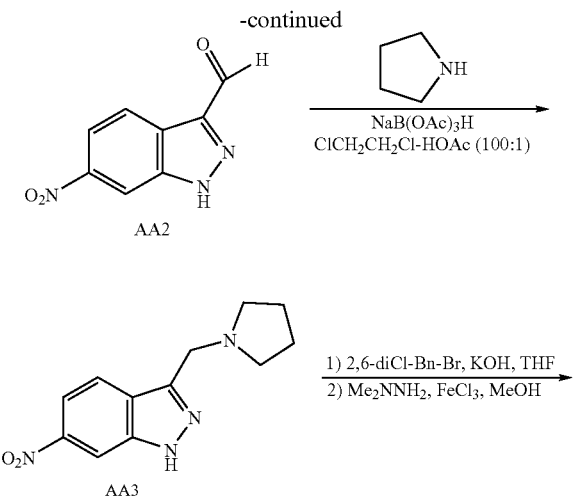

Alternatively, the antagonists of the present invention may also be prepared via solid-phase methods as represented by the synthesis of 2 and 3 (Schemes AB and Scheme AC, respectively). In Scheme AB, N-□-Fmoc-N-□-Boc-2,4-di-aminobutyric acid (AB1) was coupled with benzyl amine in the presence of DCC and HOBt. The resulting benzylamide was treated with TFA in DCM to give AB2, which was then loaded onto 2-Cl-trityl-Cl resin in the presence of DIEA to afford AB3. Deprotection of Fmoc group in AB3 with piperidine was followed by coupling with Fmoc-4-Cl-Phe-OH in the presence of HBTU and HOBt. The resulting coupled product was deprotected again with piperidine to afford the resin-bound dipeptide amine AB4. Urea formation between AB4 and aminoindazole intermediate AA4 was accomplished by using 4-nitrophenylchloroformate to provide AB5, which was cleaved with TFA to afford target 2.

Similarly, Scheme AC described a solid-phase synthesis of the antagonists having an amine group at carboxy-terminus of the $A_2$, such as 3 and 6, by mono-attaching a di-amine, such as ethylenediamine, on 2-Cl-trityl-Cl resin followed by coupling with the protected amino acid $A_2$ and then $A_1$ to furnish the required resin-bound dipeptide amine such as AC4.

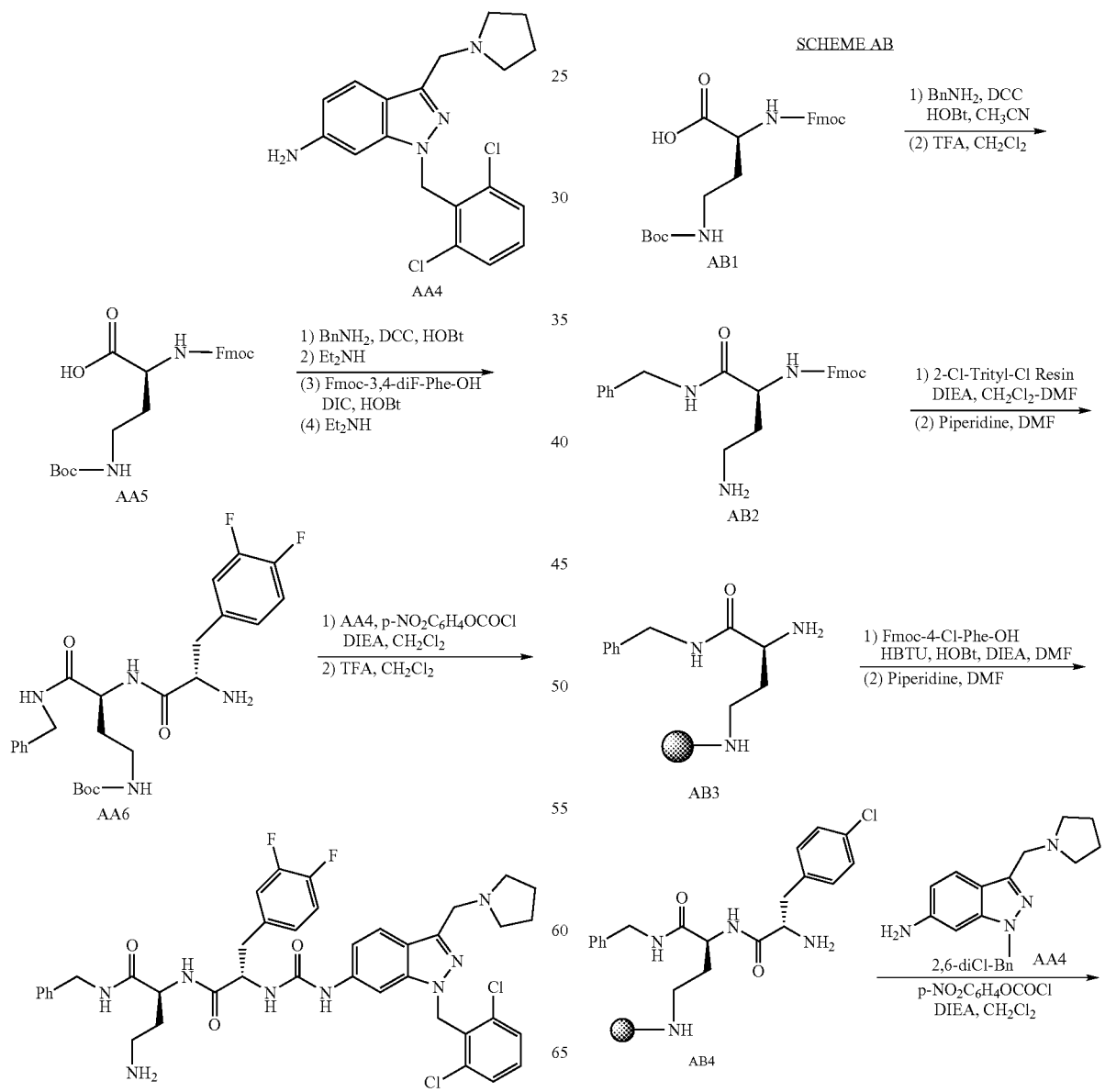

-continued
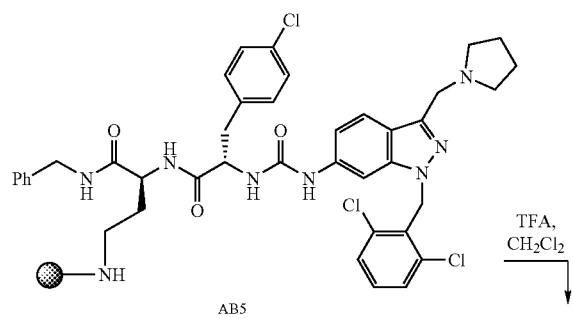
AB5
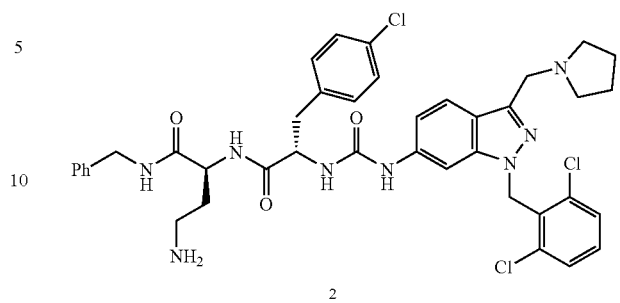
2
TFA, CH$_2$Cl$_2$
SCHEME AC
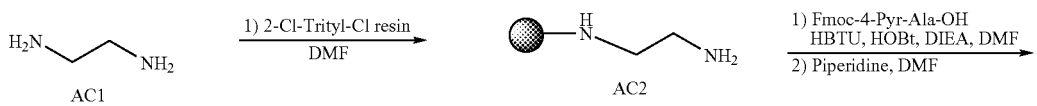
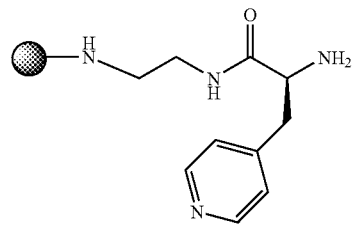
AC3
1) Fmoc-3,4-diF-Phe-OH
   HBTU, HOBt, DIEA, DMF
2) Piperidine, DMF
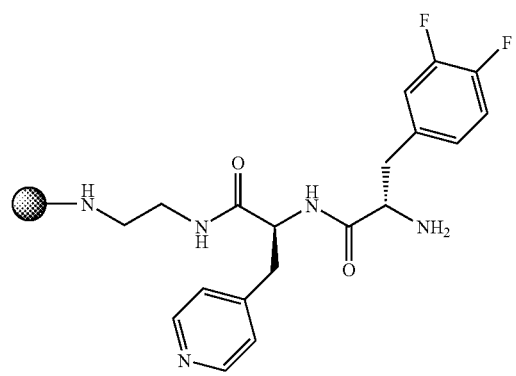
AC4
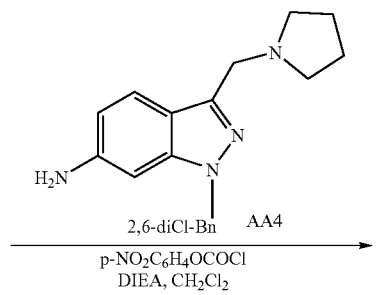
AA4
2,6-diCl-Bn
p-NO$_2$C$_6$H$_4$OCOCl
DIEA, CH$_2$Cl$_2$
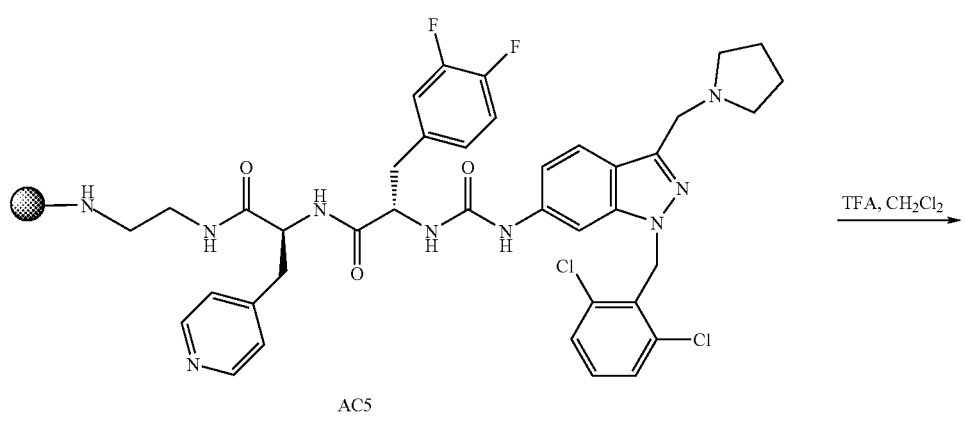
AC5
TFA, CH$_2$Cl$_2$ -continued

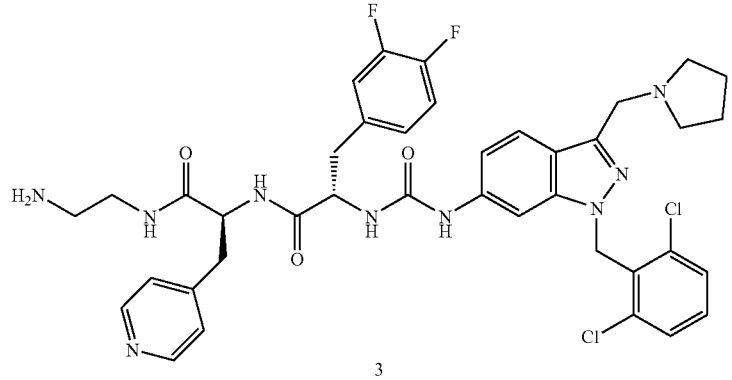

3

The side-chain amine in antagonists such as 1 and 3 may be converted to other functional groups such as acetamidine and guanidine by using standard procedures. For example, the acetamidine and guanidine groups can be introduced by treating the side-chain amine with S-2-naphthylmethyl thioacetimidate hydrobromide and 2-methyl-2-thiopseudourea, respectively.

The thioureidoindoles [X=S, general formula (I)] may be prepared as described hereinafter. Aminoindazole substrate is reacted with thiocarbonyldiimidazole in a chlorinated solvent and then the imidazole by-product filtered from the solution. The solution than can be concentrated to afford the N-imidazolyl-N'-aminoindazolyl-thiourea. This intermediate is then reacted with a peptide amine in a polar, aprotic solvent with heating (80-100 degrees) to afford the N-peptido-N'-aminoindazolyl-thiourea product.

Amidoindazoles [p=0, X=O, general formula (I)] may be prepared from a dipeptide amine AAG6 (Scheme AAGeneric) and an indazole carboxylic acid intermediate by using standard coupling conditions such as DCC/HOBt. The required indazole carboxylic acid intermediates can be prepared from the appropriately indole carboxylic acid esters by using the same method as described for aminoindazole intermediate AAG4 in Scheme AAGeneric.

Carbon-chain extension from n=1 to n=2 at the 3-position of the indazole [see general formula (I)] may be introduced in the intermediate AAG2 (Scheme AAGeneric) via aldehyde-nitromethane condensation followed by reduction of the resulting α,β-unsaturated nitro compounds to saturated amine.

The utility of the compounds to treat PAR-1 mediated disorders (e.g., thrombotic disorders) can be determined according to the procedures described herein. The present invention therefore provides a method of treating PAR-1 mediated disorders (e.g., thrombotic disorders) in a subject in need thereof which comprises administering any of the compounds as defined herein in a quantity effective to treat PAR-1 mediated disorders. The compound may be administered to a patient by any conventional route of administration, including, but not limited to, intravenous, oral, subcutaneous, intramuscular, intradermal and parenteral.

The present invention also provides pharmaceutical compositions comprising one or more compounds of this invention in association with a pharmaceutically acceptable carrier.

To prepare the pharmaceutical compositions of this invention, one or more compounds of formula (I) or salt thereof of the invention as the active ingredient, is intimately admixed with a pharmaceutical carrier according to conventional pharmaceutical compounding techniques, which carrier may take a wide variety of forms depending on the form of preparation desired for administration, e.g., oral or parenteral such as intramuscular. In preparing the compositions in oral dosage form, any of the usual pharmaceutical media may be employed. Thus, for liquid oral preparations, such as, for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, from about 0.03 mg/kg to about 100 mg/kg (preferred from about 0.1 mg/kg to about 30 mg/kg) of a compound of the present invention and may be given at a dosage from about 0.1 mg/kg/day to about 300 mg/kg/day (preferred from about 1 mg/kg/day to about 50 mg/kg/day). The dosages, however, may be varied depending upon the requirement of the patients, the severity of the condition being treated and the compound being employed. The use of either daily administration or post-periodic dosing may be employed.

Preferably these compositions are in unit dosage forms such as tablets, pills, capsules, powders, granules, sterile parenteral solutions or suspensions, metered aerosol or liquid sprays, drops, ampoules, autoinjector devices or suppositories for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums and other pharmaceutical diluents, e.g. water, to form a solid preformulation composition containing a homogeneous mixture of a compound of the present invention or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 0.1 mg to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their components enantiomers by standard techniques, such as the formation of diastereomeric pairs by salt formation with an optically active acid, such as (−)-di-p-toluoyl-d-tartaric acid and/or (+)-di-p-toluoyl-1-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The method of treating PAR-1 mediated disorders (e.g., thrombotic disorders) described in the present invention may also be carried out using a pharmaceutical composition comprising any of the compounds as defined herein and a pharmaceutically acceptable carrier. The pharmaceutical composition may contain between about 0.01 mg to about 100 mg, preferably from about 5 to about 50 mg, of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl cellulose and the like. For parenteral administration, sterile suspensions and solutions are desired. Isotonic preparations which generally contain suitable preservatives are employed when intravenous administration is desired.

The compound of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residue. Furthermore, the compounds of the present invention may be coupled to a class of biodegradable polymers useful in achieving controlled release of a drug, for example, polylactic acid, polyepsilon caprolactone, polyhydroxy butyeric acid, polyorthoesters, polyacetals, polydihydropyrans, polycyanoacrylates and cross-linked or amphipathic block copolymers of hydrogels.

Compounds of this invention may be administered in any of the foregoing compositions and according to dosage regimens established in the art whenever treatment of PAR-1 mediated disorders is required.

The daily dosage of the products may be varied over a wide range from about 0.01 mg to about 1,000 mg per adult human per day. For oral administration, the compositions are preferably provided in the form of tablets containing about 0.01, 0.05, 0.1, 0.5, 1.0, 2.5, 5.0, 10.0, 15.0, 25.0, 50.0, 100, 150, 200, 250 and 500 mg of the active ingredient for the symptomatic adjustment of the dosage to the patient to be treated. An effective amount of the drug is ordinarily supplied at a dosage level of from about 0.01 mg/kg to about 100 mg/kg of body weight per day. Preferably, the range is from about 0.03 mg/kg to about 10 mg/kg of body weight per day. The compounds may be administered on a regimen of about 1 time to about 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

Biology

The compounds of the present invention are thrombin receptor (PAR-1) antagonists. The compounds interrupt platelet activation induced by thrombin's proteolytic cleavage of its platelet surface receptor, and thereby inhibit platelet aggregation. Such compounds are, therefore, useful in treating platelet-mediated thrombotic disorders (e.g., arterial and venous thrombosis, acute myocardial infarction, reocclusion following thrombolytic therapy and angioplasty, and a variety of vaso-occlusive disorders) and other PAR-1 mediated disorders.

In Vitro Thrombin Receptor Binding Assay

CHRF membranes (Jones, *Biochim. Biophys. Acta* 1992, 1136, 272) are thawed from −70° C., centrifuged at maximum speed for 5 min, washed twice with binding buffer (50 mM HEPES containing 5 mM $MgCl_2$ and 0.1% BSA), and resuspended in binding buffer (25 µg/100 mL). 100 µL of membranes are added to the 24-Wallac plates and delivered to the Tomtech apparatus. In a typical experiment, 6 µL of samples (from a 125 µg/mL intermediary plate, 20% DMSO) and 44 µL buffer are delivered to the plates (final conc. of compounds is 3.7 µg/mL, 0.6% DMSO). Similarly, 6 µL 20% DMSO and 44 µL buffer are delivered to both column 1 (NSB) and column 12 (TB). 10 mL Ser-pFPhe-Har-Leu-Har-Lys-Tyr-$NH_2$ (SEQ. ID. No. 2) (721-40; 500 µM in deionized water) is added to column 1. 50 µL tritiated 721-40 (specific activity 46 Ci/mmol) is added to all the wells. The plates are mixed well for 20 seconds, incubated for 30 min, and then harvested with 10 mM HEPES/138 mM NaCl using the Skatron harvester. The filters (GF/C Brandel FPXLR 296) are presoaked 3 h in 0.5% polyethylenimine in HEPES/0.1M N-acetylglucosamine) are set in Saran™ wrap and dried for 3 min in the microwave, and placed in sample bags (Wallac 1450-432). 4.5 mL scintillation fluid (Wallac, Betaplate Scint 1205-440) is added. The bags are sealed, placed in filter cassettes (Wallac 1450-104), and analyzed on the microbeta counter.

In Vitro Inhibition Of Thrombin-Induced Gel-Filtered Platelet Aggregation Assay

The percentage of platelet aggregation is calculated as an increase in light transmission of compound-treated platelet concentrate vs. control-treated platelet concentrate. Human blood is obtained from drug free, normal donors in tubes containing 0.13M sodium citrate. Platelet rich plasma (PRP) is collected by centrifugation of whole blood at 200×g for 10 min at 25° C. The PRP (5 mL) is gel filtered through Sepharose 2B (bed volume 50 mL), and the platelet count is adjusted to $2 \times 10^7$ platelets per sample. The following constituents are added to a siliconized cuvette: concentrated platelet filtrate and Tyrode's buffer (0.14M NaCl, 0.0027M KCl, 0.012M $NaHCO_3$, 0.76 mM $Na_2HPO4$, 0.0055M glucose, 2 mg/mL BSA and 5.0 mM HEPES @ pH 7.4) in an amount equal to 350 µL, 50 µL of 20 mM calcium and 50 µL of the test compound. Aggregation is monitored in a BIODATA aggregometer for the 3 min following the addition of agonist (thrombin 50 µL of 1 unit/mL).

Table 1 shows the biological activity of the compounds of the present invention. Table 1 contains $IC_{50}$ values (µM) of the compounds against platelet aggregation stimulated by thrombin and $IC_{50}$ values (µM) in a thrombin receptor (PAR-1) binding assay.

EXAMPLES

General Procedures: Resins and protected amino acids were purchased from Novabiochem, Bachem Bioscience, Advanced ChemTech or Synthe Tech. All other chemicals were obtained from commercial suppliers and used without further purification. $^1H$ and $^{13}C$ NMR spectra were recorded on a Bruker AC 300B (300 MHz proton) or a Bruker AM-400 (400 MHz proton) spectrometer with $Me_4Si$ as an internal standard (s=singlet, d=doublet, t=triplet, br=broad). APCI-MS and ES-MS were recorded on a VG Platform II mass spectrometer; methane was used for chemical ionization, unless noted otherwise. Accurate mass measurements were obtained by using a VG ZAB 2-SE spectrometer in the FAB mode. TLC was performed with Whatman 250-µm silica gel plates. Preparative TLC was performed with Analtech 1000-µm silica gel GF plates. Flash column chromatography was conducted with flash column silica gel (40-63 µm) and column chromatography was conducted with standard silica gel. HPLC separations were carried out on three Waters PREP-PAK® Cartridges (25×100 mm, BONDAPAK® C18, 15-20 µm, 125 Å) connected in series; detection was at 254 nm on a Waters 486 UV detector. Analytical HPLC was carried out on a Supelcosil ABZ+PLUS column (5 cm×2.1 mm), with detection at 254 nm on a Hewlett Packard 1100 UV detector. Microanalysis was performed by Robertson Microlit Laboratories, Inc.

In the examples and throughout this application, the following abbreviations have the meanings recited hereinafter:

Ac Acetyl

ACN Acetonitrile

Bn Benzyl

Boc t-Butoxycarbonyl

DCC 1,3-Dicyclohexylcarbodiimide

DCM Dichloromethane

DIC Diisopropylcarbodiimide

DIEA Diisopropylethylamine

DMF N,N-Dimethylformamide

Et Ethyl

EtOAc Ethyl acetate

Fmoc 9-Fluorenylmethoxycarbonyl h Hour

HBTU 2-(1H-Benzotriazole-1-yl)-1,1,3,3-tetramethyluronium hexafluorophosphate

HOAc Acetic acid

HOBT Hydroxybenzotriazole

Me Methyl min Minute rt room temperature

THF Tetrahydrofuran

TFA Trifluoroacetic acid

TLC Thin layer chromatography

Example 1

Synthesis of Compound 1 (Scheme AA)

Benzenepropanamide, N-[(1S)-3-amino-1-[[(phenylmethyl)amino]carbonyl]propyl]-α-[[[[[1-(2,6-dichlorophenyl)methyl]-3-(1-pyrrolidinylmethyl)-1H-indazol-6-yl]amino]carbonyl]amino]-3,4-difluoro-,(αS)-
(Compound 1)

6-Nitroindole (AA1, 1.0 g, 6.2 mmol) was suspended in a solution of sodium nitrite (4.3 g, 62 mmol) in $H_2O$ (123 mL). To the suspension 6N HCl was added slowly until the pH was about pH 1. The resulting mixture was stirred at about rt, with protection from light, for about 2.5 h and extracted with EtOAc (120 mL×3). The combined extracts were washed with $H_2O$ (50 mL), brine (50 mL), dried ($Na_2SO_4$) and evaporated to give 1.13 g of indazole AA2 as a yellow-pink solid. A solution of AA2 (450 mg, 2.4 mmol) and pyrrolidine (836 mg, 11.8 mmol) in $ClCH_2CH_2Cl$:DMF:HOAc (90:9:1) were stirred at about rt for about 20 min, to which was then added $NaB(OAc)_3H$ (1.25 g, 5.9 mmol) in one portion. The mixture was stirred at about rt for about 1 h, and then diluted with EtOAc (200 mL), washed with saturated $NaHCO_3$ (30 mL), brine (30 mL), dried ($Na_2SO_4$) and evaporated to afford 570 mg of AA3 as a viscous brown solid. 6-Nitroindazole AA3 (4.4 g, 17.8 mmol) was dissolved in dry THF (200 mL) under argon and 2,6-dichlorobenzyl bromide (4.3 g, 17.8 mmol) was added, followed by portionwise addition of pulverized KOH (1.17 g, 17.8 mmol) over about the next 20 min. The reaction was stirred at about rt for about 1 h and then evaporated in vacuo to an oil, which was partitioned between ethyl acetate (500 mL) and water (100 mL). The organic layer was separated and washed twice with water, three times with brine, dried ($Na_2SO_4$) and evaporated in vacuo to a brown solid. This was purified by flash column chromatography using DCM:MeOH (19:1) to afford 2.4 g of a tan solid which was combined with ferric chloride hexahydrate (0.30 g, 1.1 mmol) and activated charcoal (3.0 g, 0.25 mmol) in MeOH (200 mL). Dimethyl hydrazine (32 g, 0.53 mmol) was added and the reaction was refluxed for about 2 h, cooled to about rt and filtered through dicalite, which was washed several times with DCM:MeOH (4:1). The combined filtrates were evaporated in vacuo to a brown solid, which was purified by flash chromatography with DCM:MeOH:$NH_4OH$ (90:8:1) to give 1.75 g of amine AA4.

Fmoc-α-N-Boc-γ-N-diaminobutyric acid AA5 (10.8 g, 24.5 mmol) was stirred in ACN (300 mL) under argon as HOBT (3.75 g, 24.4 mmol) was added, followed by benzylamine (2.6 g, 24.3 mmol). DCC (10.4 g, 48.7 mmol) was added and the reaction was stirred at about rt for about 3 h, whereupon the resulting white solid was filtered and washed with cold ACN (14.4 g). The solid was stirred in ACN (500 mL) containing diethyl amine (25 mL) for about 2 h and a little solid was filtered; the filtrate was evaporated in vacuo to an oil, which was triturated three times with hexane (400 mL each) to a white solid. The solid was dissolved in ACN (400 mL) and HOBT (2.9 g, 19.1 mm) and Fmoc-3,4 difluorophenylalanine (8.1 g, 19.1 mmol) were added, followed by DIC (4.81 g, 38.2 mmol) and stirred at about rt for about 16 h. The reaction was cooled in an ice bath and the white solid was filtered and washed with cold ACN. The solid was stirred in ACN (350 mL) containing diethylamine (35 mL) for about 5 h and evaporated in vacuo to a white solid, which was triturated three times with hexane, dissolved in chloroform (250 mL), dried ($Na_2SO_4$) and evaporated in vacuo to a white solid AA6 (8.0 g).

6-Aminoindazole AA4 (1.9 g, 5.0 mmol) and diisopropyl ethylamine (3.2 g, 25 mmol) in DCM (225 mL) under argon were cooled to about $-20°$ C. with $CCl_4$/dry ice bath; 4-nitrophenyl chloroformate (1.10 g, 5.5 mmol) dissolved in DCM (10 mL) was added and the reaction was stirred at about $-20°$ C. for about 30 min. The dipeptide AA6 (3.05 g, 5.0 mmol) was added and after about 30 min the reaction was allowed to warm to about rt and stirred for about an additional 6 h. The solution was ice bath cooled; a yellow solid was filtered and then washed with fresh, cold DCM. The solid was added to a solution (100 mL) of DCM:TFA:anisole (50:50:1), stirred at about rt for about 2.0 h and then evaporated in vacuo to a solid, which was triturated with diethyl ether (4×). The solid was purified by flash column chromatography using DCM:MeOH:$NH_4OH$ (80:16:2) to give compound 1 as a white solid. The product was converted to the hydrochloride salt by dissolution in ACN and 1N HCl (20 mL, 1:1); evaporation in vacuo (3×) and then lyophilization overnight afforded the white flaky solid Compound 1.HCl: $^1H$ NMR ($CD_3OD$) δ 7.99 (s, 1H), 7.72 (d, J=8.4 Hz, 1H), 7.45-7.05 (m, 12 H), 5.62 (s, 2H), 4.64 (s, 2H), 4.50 (m, 2H), 4.39 (d, J=2.6 Hz, 2H), 3.52 (m, 2H), 3.30-2.95 (m, 6H), 2.30-1.85 (m, 6H); ES-MS m/z 791 ($MH^+$); Anal. Calc. $C_{40}H_{42}Cl_2F_2N_8O_3$.2HCl.2$H_2O$ (900.68): C, 53.34; H, 5.37; N, 12.44; Cl, 15.74; KF, 4.00. Found: C, 53.15; H, 5.45; N, 12.38; Cl, 15.89; KF, 3.62.

Example 2

Synthesis of Compound 2 (Scheme AB)

Benzenepropanamide, N-[(1S)-3-amino-1-[[(phenylmethyl)amino]carbonyl]propyl]-α-[[[[[1-(2,6-dichlorophenyl)methyl]-3-(1-pyrrolidinylmethyl)-1H-indazol-6-yl]amino]carbonyl]amino]-4-chloro-, (αS)-
(Compound 2)

To a solution of N-α-Fmoc-N-γ-Boc-diaminobutyric acid (AB1, 4.0 g, 9.1 mmol), $BnNH_2$ (1.07 g, 10 mmol) in $CH_3CN$ (150 mL) was added HOBt (1.85 g, 13.7 mmol) and DCC (2.82 g, 13.7 mmol). The mixture was stirred at rt for 2.5 h, at which time TLC indicated that reaction was complete. The resulting white precipitates were collected by filtering and washing with $CH_3CN$ to give 5.0 g of product (a mixture of the desired product and dicyclohexylurea). The combined filtrates were concentrated under vacuo and the residue was dissolved in EtOAc (150 mL). The solution was washed with saturated $NaHCO_3$, $H_2O$, brine, dried ($Na_2SO_4$), and evaporated to give a white powder which was recrystallized from $CH_3CN$ to afford an additional product (1.7 g). The combined crude products were treated with 50% TFA in $CH_2Cl_2$ (80 mL) at rt for 1 h. The volatiles were removed under vacuo, and the residue was triturated with $Et_2O$ to give AB2 as a colorless solid (6.3 g). $^1H$ NMR showed it was a mixture AB2 and dicyclohexylurea (ration 1:1.4). To a solution of the crude AB2 (6.16 g, 7.14 mmol) and DIEA (2.71 g, 21.0 mmol) in DCM-DMF (1:1, 120 mL) was added 2-chlorotrityl chloride resin (4.0 g, 4.2 mmol) and the suspension was stirred at ambient temperature for 20 h. The reaction mixture was filtered on a sintered glass funnel and washed with DMF (2×), MeOH (3×), DCM (3×) and dried in vacuo to give resin (5.0 g). 4.9 g of resin was treated with 20% piperidine in DMF (80 mL) at rt for 2 h and then filtered, washed with DMF (2×), MeOH (2×), DCM (2×), $Et_2O$ (2×) and dried in vacuo to afford resin AB3 (4.15 g, loading level=0.81 mmol/g, based on the mass loss during removing Fmoc group). A portion of AB3 (1.1 g, 0.89 mmol) was suspended in DMF (30 mL) and treated with Fmoc-4-Cl-Phe-OH (0.94 g, 2.2 mmol), HOBT (0.30 g, 2.2 mmol), DIEA (0.58 g, 4.5 mmol), and HBTU (0.85 g, 2.2 mmol). The suspension was stirred at rt for 20 h and then filtered, washed with DMF, MeOH and DCM. The resulting resin was treated with 20% piperidine in DMF (30 mL) at rt for 2 h and then filtered, washed with DMF (2×), MeOH (2×), DCM (2×) and Et$_2$O (2×) to afford resin AB4 (1.24 g). 6-Aminoindazole AA4 (30 mg, 0.08 mmol) and diisopropyl ethylamine (52 mg, 0.4 mmol) in DCM (3 mL) under argon were cooled to about −20° C. with CCl$_4$/dry ice bath; 4-nitrophenyl chloroformate (17 mg, 0.085 mmol) dissolved in DCM (1 mL) was added dropwise and the reaction was stirred at about −20° C. for about 15 min. The resin-bound dipeptide amine AB4 (47 mg, 0.034 mmol) was added and after about 20 min the reaction was allowed to warm to about rt and stirred for about an additional 2.5 h. The suspension was filtered and washed with MeOH, DCM and Et$_2$O and dried in vacuo to give resin AB5, which was then cleaved with TFA/DCM/anisole (50:50:1, 5 mL) at rt for 1.5 h, and reaction mixture was filtered and washed with fresh 30% TFA in DCM. The filtrates were combined and evaporated in vacuo, and the residue was purified by preparative TLC using DCM-MeOH-28% NH$_4$OH (80:17:3) to give 2 as a gray solid: $^1$H NMR (CD$_3$OD) δ 7.91 (s, 1H), 7.68 (d, J=8.8 Hz, 1H), 7.45-7.17 (m, 12H), 7.00 (d, J=7.6 Hz, 1H), 5.59 (s, 2H), 4.55-4.36 (m, 6H), 3.17-2.96 (m, 8H), 2.21-1.90 (m, 6H); ES-MS m/z 789 (MH$^+$).

Example 3

Synthesis of Compound 3 (Scheme AC)

L-Alaninamide, 3,4-difluoro-N-[[[1-[(2,6-dichlorophenyl)methyl]-3-(1-pyrrolidinylmethyl)-1H-indazol-6-yl]amino]carbonyl]-L-phenylalanyl-N-(2-aminoethyl)-3-(4-pyridinyl)-(Compound 3)

2-Chlorotrityl chloride resin (4.8 g, 8.65 mmol; Advanced ChemTech) was stirred in DMF (100 mL) as ethylene diamine AC1 (15.6 g, 260 mmol) was added in and reaction stirred at ambient temperature for 16 h. The resin AC2 was filtered on a sintered glass funnel and washed with DMF (4×), MeOH (3×), and DCM (3×) and dried in vacuo. A portion of resin AC2 (2.0 g, 3.5 mmol) was placed in a solid phase hour-glass reactor and agitated (nitrogen bubbling) in DMF (40 mL) with Fmoc-4-pyridyl alanine (3.9 g, 10 mmol), HOBT (1.53 g, 10 mmol), and DIC (1.26 g, 10 mmol) for 16 h. The solution was drawn off and the resin was washed with DMF (4×), DCM (4×) and DMF (2×) and then combined with 20% piperidine in DMF (25 mL) and agitated for 1.5 h. The solution was drained and the resin AC3 was washed with DMF (SX) and agitated in DMF (20 mL) with Fmoc-3,4-diF-Phe-OH (4.23 g, 10 mmol), HOBT (1.53 g, 10 mmol) and DIC (1.26 g, 10 mmol) at ambient temperature for 16 h. The solution was removed and the resin was washed with DMF (5×), MeOH (3×), DCM (3×) and DMF (2×) and then combined with 20% piperidine in DMF (25 mL) and agitated for 1 h. The solution was drained and the resin was washed with DMF (4×), and DCM (4×) and dry DCM (3×) and stored in vacuo to give AC4. 6-Aminoindazole AA4 (75 mg, 0.20 mmol) and diisopropyl ethylamine (145 mg, 1.1 mmol) in DCM (7 mL) under argon were cooled to about −20° C. with CCl$_4$/dry ice bath; 4-nitrophenyl chloroformate (38 mg, 0.19 mmol) dissolved in DCM (2 mL) was added dropwise and the reaction was stirred at about −20° C. for about 20 min. The resin-bound dipeptide amine AC4 (110 mg) was added and after about 20 min the reaction was allowed to warm to about rt and stirred for about an additional 18 h. The suspension was filtered and washed with MeOH, DCM and Et$_2$O and dried in vacuo to give resin AC5, which was then cleaved with TFA/DCM/anisole (50:50:1, 6 mL) at rt for 1 h, and reaction mixture was filtered and washed with fresh 30% TFA in DCM. The filtrates were combined and evaporated in vacuo, and the residue was purified by preparative TLC using DCM-MeOH-28% NH$_4$OH (85:12:3) to give compound 3 as a gray solid: ES-MS m/z 792 (MH$^+$).

Example 4

As a specific embodiment of an oral composition, 100 mg of the Compound 1 of Example 1 is formulated with sufficient finely divided lactose to provide a total amount of about 580 mg to about 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A compound of the following formula (I):

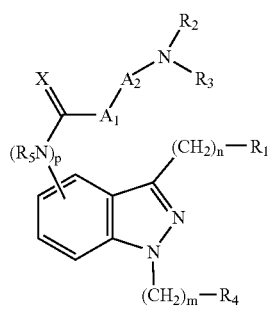

wherein:

$A_1$ and $A_2$ are each independently a D- or L-amino acid selected from the group consisting of alanine, β-alanine, arginine, homoarginine, cyclohexylalanine, citrulline, cysteine (optionally substituted with $C_1$-$C_4$ alkyl, aryl, or ar$C_1$-$C_4$ alkyl), 2,4-diaminobutyric acid (optionally substituted with acyl, $C_1$-$C_4$ alkyl, aroyl, amidino, or MeC(NH)-), 2,3-diaminopropionic acid (optionally substituted with acyl, $C_1$-$C_4$ alkyl, aroyl, amidino, or MeC(NH)-), glutamine, glycine, indanylglycine, lysine (optionally substituted with acyl, $C_1$-$C_4$ alkyl, aroyl, MeC(NH)-), valine, methionine, proline, serine (optionally substituted with $C_1$-$C_4$ alkyl, aryl, or ar$C_1$-$C_4$ alkyl), homoserine (optionally substituted with $C_1$-$C_4$ alkyl, aryl, or ar$C_1$-$C_4$ alkyl), tetrahydroisoquinoline-3-COOH, threonine (optionally substituted with $C_1$-$C_4$ alkyl, aryl, or ar$C_1$-$C_4$ alkyl), ornithine (optionally substituted with acyl, $C_1$-$C_4$ alkyl, aroyl, MeC(NH)-), and an unsubstituted or substituted aromatic amino acid selected from the group consisting of phenylalanine, heteroarylalanine, naphthylalanine, homophenylalanine, histidine, tryptophan, tyrosine, arylglycine, heteroaryiglycine, aryl-β-alanine, and heteroaryl-β-alanine wherein the substituents on the aromatic amino acid are independently selected from the group consisting of halogen, $C_1$-$C_4$ alkyl, $C_1$-$C_4$ alkoxy, hydroxy, $C_1$-$C_4$ alkoxycarbonyl, amino, amidino, guanidino, fluorinated $C_1$-$C_4$ alkyl, fluorinated $C_1$-$C_4$ alkoxy, $C_1$-$C_4$ alkylsulfonyl, $C_1$-$C_4$ alkylcarbonyl, cyano, aryl, heteroaryl, ar$C_1$-$C_4$ alkyl, $C_2$-$C_4$ alkenyl, alkynyl, and -nitro;

$R_1$ is selected from the group consisting of amino, $C_1$-$C_8$ alkylamino, $C_1$-$C_8$ dialkylamino, arylamino, ar$C_1$-$C_8$ alkylamino, $C_3$-$C_8$ cycloalkylamino, heteroalkyl$C_1$-$C_8$ alkylamino, heteroalkyl$C_1$-$C_8$ alkyl-N-methylamino, $C_1$-$C_8$ dialkylamino$C_1$-$C_8$ alkylamino, —N($C_1$-$C_8$alkyl)-$C_1$-$C_8$ alkyl—N($C_1$-$C_8$alkyl)$_2$, N($C_1$-$C_8$alkyl)($C_1$-$C_8$alkenyl), —N($C_1$-$C_8$alkyl)($C_3$-$C_8$cycloalkyl), heteroalkyl and substituted heteroalkyl wherein the substituent on the heteroalkyl is selected from the group consisting of oxo, amino, $C_1$-$C_8$ alkoxy$C_1$-$C_8$ alkyl, $C_1$-$C_8$ alkylamino and $C_1$-$C_8$ dialkylamino;

$R_2$ and $R_3$ are each independently selected from the group consisting of hydrogen, $C_1$-$C_8$ alkyl, $C_3$-$C_8$ cycloalkyl, $C_3$-$C_8$ cycloalkyl$C_1$-$C_8$ alkyl, aryl, heteroalkyl, substituted heteroalkyl (wherein the substituent on the heteroalkyl is one or more substituents independently selected from the group consisting of $C_1$-$C_8$ alkoxycarbonyl, $C_1$-$C_8$ alkyl, or and $C_1C_4$ alkylcarbonyl), heteroalkyl$C_1$-$C_8$ alkyl, indanyl, acetamidino$C_1$-$C_8$ alkyl, amino$C_1$-$C_8$ alkyl, $C_1$-$C_8$ alkylamino$C_1$-$C_8$ alkyl, $C_1$-$C_8$ dialkylamino$C_1$-$C_8$ alkyl, unsubstituted or substituted heteroaryl$C_1$-$C_8$ alkyl and unsubstituted or substituted ar$C_1$-$C_8$ alkyl, wherein the substituent on the aralkyl or heteroarylalkyl group is one or more substituents independently selected from the group consisting of halogen, nitro, amino, $C_1$-$C_8$ alkyl, $C_1$-$C_8$ alkoxy, hydroxy, cyano, $C_1$-$C_4$ alkylcarbonyl, $C_1$-$C_8$ alkoxycarbonyl, hydroxy$C_1$-$C_8$ alkyl and aminosulfonyl; or $R_2$ and $R_3$, together with the nitrogen to which they are attached, alternatively form an unsubstituted or substituted heteroalkyl group selected from the group consisting of piperidinyl, piperazinyl, morpholinyl or and pyrrolidinyl, wherein the substituent is one or more substituents independently selected from the group consisting of $C_1$-$C_8$ alkyl $C_1$-$C_8$ alkoxycarbonyl or and $C_1$-$C_4$ alkylcarbonyl;

$R_4$ is selected from the group consisting of unsubstituted or substituted aryl, ar$C_1$-$C_8$ alkyl, $C_3$-$C_8$ cycloalkyl, and heteroaryl, where the substituents on the aryl, ar$C_1$-$C_8$ alkyl, cycloalkyl or heteroaryl group are independently selected from the group consisting of halogen, nitro, amino, cyano, hydroxyalkyl, $C_1$-$C_8$ alkyl, $C_1$-$C_8$ alkoxy, hydroxy, $C_1$-$C_4$ alkylcarbonyl, $C_1$-$C_8$ alkoxycarbonyl, fluorinated $C_1$-$C_4$ alkyl, fluorinated $C_1$-$C_4$ alkoxy, and $C_1$-$C_4$ alkylsulfonyl;

$R_5$ is selected from the group consisting of hydrogen and sulfur;

m is an integer selected from the group consisting of 0, 1, 2 and 3;

n is an integer selected from the group consisting of 1 and 2; and p is an integer selected from the group consisting of 0 and 1;

and pharmaceutically acceptable salts thereof.

2. A pharmaceutical composition comprising a pharmaceutically acceptable carrier and a compound of claim 1.

3. A pharmaceutical composition made by mixing a compound of claim 1 and a pharmaceutically acceptable carrier.

4. The compound of claim 1, wherein:

$A_1$ and $A_2$ are each independently an L-amino acid selected from the group consisting of alanine, β-alanine, arginine, homoarginine, cyclohexylalanine, citrulline, cysteine (optionally substituted with $C_1$-$C_4$ alkyl, aryl, or $arC_1$-$C_4$ alkyl), 2,4-diaminobutyric acid (optionally substituted with acyl, $C_1$-$C_4$ alkyl, aroyl, amidino, or MeC(NH)-), 2,3-diaminopropionic acid (optionally substituted with acyl, $C_1$-$C_4$ alkyl, aroyl, amidino, or MeC(NH)-), glutamine, glycine, indanylglycine, lysine (optionally substituted with acyl, $C_1$-$C_4$ alkyl, aroyl, MeC(NH)-), valine, methionine, proline, serine (optionally substituted with $C_1$-$C_4$ alkyl, aryl, or $arC_1$-$C_4$ alkyl), homoserine (optionally substituted with $C_1$-$C_4$ alkyl, aryl, or $arC_1$-$C_4$ alkyl), tetrahydroisoquinoline-3-COOH, threonine (optionally substituted with $C_1$-$C_4$ alkyl, aryl, or $arC_1$-$C_4$ alkyl), ornithine (optionally substituted with acyl, $C_1$-$C_4$ alkyl, aroyl, MeC(NH)-), and an unsubstituted or substituted aromatic amino acid selected from the group consisting of phenylalanine, heteroarylalanine, naphthylalanine, homophenylalanine, histidine, tryptophan, tyrosine, arylglycine, heteroarylglycine, aryl-β-alanine, and heteroaryl-β-alanine wherein the substituents on the aromatic amino acid are independently selected from the group consisting of halogen, $C_1$-$C_4$ alkyl, $C_1$-$C_4$ alkoxy, hydroxy, $C_1$-$C_4$ alkoxycarbonyl, amino, amidino, guanidino, fluorinated $C_1$-$C_4$ alkyl, fluorinated $C_1$-$C_4$ alkoxy, $C_1$-$C_4$ alkylsulfonyl, $C_1$-$C_4$ alkylcarbonyl, cyano, aryl, heteroaryl, $arC_1$-$C_4$ alkyl, $C_2$-$C_4$ alkenyl, alkynyl, and nitro; $R_1$ is selected from the group consisting of amino, $C_1$-$C_6$ alkylamino, $C_1$-$C_6$ dialkylamino, arylamino, $arC_1$-$C_6$ alkylamino, heteroalkyl$C_1$-$C_6$ alkylamino, —N($C_1$-$C_6$alkyl)-$C_1$-$C_6$ alkyl—N($C_1$-$C_6$alkyl)$_2$, heteroalkyl and substituted heteroalkyl wherein the substituent on the heteroalkyl is selected from the group consisting of oxo, amino, $C_1$$C_6$alkoxy$C_1$$C_6$ alkyl, $C_1$-$C_6$ alkylamino and $C_1$-$C_6$ dialkylamino;

$R_2$ is selected from the group consisting of hydrogen and $C_1$-$C_6$ alkyl;

$R_3$ is selected from the group consisting of $C_1$-$C_8$ alkyl, $C_3$-$C_6$ cycloalkyl, $C_3$$C_6$cycloalkyl$C_1$$C_6$alkyl, aryl, heteroaryl$C_1$-$C_6$ alkyl, and substituted heteroaryl$C_1$$C_6$alkyl wherein the substituent is selected from the group consisting of $C_1$-$C_4$ alkyl, heteroalkyl, heteroalkyl$C_1$-$C_6$ alkyl, indanyl, acetamidino$C_1$-$C_6$ aklcyl, amino$C_1$-$C_6$ alkyl, $C_1$$C_6$alkylamino$C_1$-$C_6$ alkyl, $C_1$-$C_6$ dialkylamino$C_1$-$C_6$ alkyl, $arC_1$-$C_8$alkyl, and substituted $arC_1$-$C_8$ alkyl (wherein the substituent on the aralkyl group is one to five substituents independently selected from the group consisting of halogen, nitro, amino, $C_1$-$C_6$ alkyl, $C_1$-$C_6$ alkoxy, $C_1$-$C_6$ alkoxycarbonyl, hydroxyalkyl and aminosulfonyl);

$R_2$ and $R_3$, together with the nitrogen to which they are attached, alternatively form an unsubstituted or substituted heteroalkyl group selected from the group consisting of piperidinyl, piperazinyl or and pyrrolidinyl, wherein the substituent is independently one or two substituents selected from $C_1$-$C_6$ alkyl;

$R_4$ is selected from the group consisting of unsubstituted or substituted aryl, $arC_1$-$C_6$ alkyl, $C_3$-$C_6$cycloalkyl and heteroaryl, where the substituents on the aryl, aralkyl, cycloalkyl or heteroaryl group are independently selected from one to three substituents selected from the group consisting of halogen, cyano, $C_1$-$C_4$ alkyl, $C_1$-$C_4$ alkoxy, $C_1$-$C_4$alkoxycarbonyl, fluorinated $C_1$-$C_4$ alkyl, fluorinated $C_1$-$C_4$ alkoxy and $C_1$-$C_4$alkylsulfonyl;

$R_5$ is hydrogen;

X is oxygen; and p is 1;

and pharmaceutically acceptable salts thereof.

5. The compound of claim 4, wherein:

$A_1$ is an L-amino acid selected from the group consisting of alanine, arginine, cyclohexylalanine, glycine, proline, tetrahydroisoquinoline-3-COOH, and an unsubstituted or substituted aromatic amino acid selected from the group consisting of phenylalanine, naphthylalanine, homophenylalanine, and O-methyl tyrosine, wherein the substituents on the aromatic amino acid are independently one to five substituents selected from the group consisting of halogen, $C_1$-$C_4$ alkyl, $C_1$-$C_4$ alkoxy, hydroxy, $C_1$-$C_4$ alkoxycarbonyl, amino, amidino, guanidino, fluorinated $C_1$-$C_4$ alkyl, fluorinated $C_1$-$C_4$ alkoxy, $C_1$-$C_4$ alkylsulfonyl, $C_1$-$C_4$ alkylcarbonyl, cyano, aryl, heteroaryl, $arC_1$-$C_4$ alkyl, $C_2$-$C_4$ alkenyl, alkynyl, and nitro;

$A_2$ is an L-amino acid selected from the group consisting of alanine, β-alanine, arginine, citrulline, cysteine (optionally substituted with a substituent selected from the group consisting of $C_1$-$C_4$ alkyl, aryl, and $arC_1$-$C_4$ alkyl), 2,4-diaminobutyric acid (optionally substituted with a substituent selected from the group consisting of acyl, $C_1$-$C_4$ alkyl, aroyl, amidino, and MeC(NH)-), 2,3-diaminopropionic acid (optionally substituted with a group selected from the group consisting of acyl, $C_1$-$C_4$ alkyl, aroyl, amidino, and MeC(NH)-), glutamine, glycine, lysine (optionally substituted with a substituent selected from the group consisting of acyl, $C_1$-$C_4$ alkyl, aroyl, and MeC(NH)-), valine, methionine, serine (optionally substituted with a substituent selected from the group consisting of $C_1$-$C_4$ alkyl, aryl, and $arC_1$-$C_4$ alkyl), homoserine (optionally substituted with a substituent selected from the group consisting of $C_1$-$C_4$ alkyl, aryl, and $arC_1$-$C_4$ alkyl), threonine (optionally substituted with a substituent selected from the group consisting of $C_1$-$C_4$ alkyl, aryl, and $arC_1$-$C_4$ alkyl), ornithine (optionally substituted with a substituent selected from the group consisting of acyl, $C_1$-$C_4$ alkyl, aroyl, and MeC(NH)-), and an unsubstituted or substituted aromatic amino acid selected from the group consisting of phenylalanine, heteroarylalanine, and histidine, wherein the substituents of the aromatic amino acid are independently one to five substituents selected from the group consisting of halogen, $C_1$-$C_4$ alkyl, $C_1$-$C_4$ alkoxy, hydroxy, $C_1$-$C_4$ alkoxycarbonyl, amino, amidino, guanidino, fluorinated $C_1$-$C_4$ alkyl, fluorinated $C_1$-$C_4$alkoxy, $C_1$-$C_4$alkylsulfonyl, $C_1$-$C_4$alkylcarbonyl, cyano, aryl, heteroaryl, $arC_1$-$C_4$ alkyl, $C_2$-$C_4$ alkenyl, alkynyl, and nitro;

$R_2$ is selected from the group consisting of hydrogen or and $C_1$-$C_4$ alkyl; and mandnare both 1;

and pharmaceutically acceptable salts thereof.

6. The compound of claim 5, wherein:

$A_1$ is an L-amino acid selected from the group consisting of alanine, arginine, cyclohexylalanine, proline, tetrahydroisoquinoline-3-COOH, and an unsubstituted or substituted aromatic amino acid selected from the group consisting of phenylalanine, naphthylalanine, homophenylalanine, and O-methyl tyrosine, wherein the substituents on the aromatic amino acid are independently one to two substituents selected from halogen, C$_1$-C$_4$ alkyl, C$_1$-C$_4$ alkoxy, hydroxy, C$_1$-C$_4$ alkoxycarbonyl, amino, amidino, guanidino, fluorinated C$_1$-C$_4$ alkyl, fluorinated C$_1$-C$_4$ alkoxy, C$_1$-C$_4$ alkylsulfonyl, C$_1$-C$_4$ alkylcarbonyl, cyano, aryl, heteroaryl, arC$_1$-C$_4$ alkyl, C$_2$-C$_4$ alkenyl, alkynyl, and nitro;

A$_2$ is an L-amino acid selected from the group consisting of alanine, β-alanine, arginine, citrulline, cysteine (optionally substituted with a substituent selected from the group consisting of C$_1$-C$_4$ alkyl, aryl, and arC$_1$-C$_4$ alkyl), 2,4-diaminobutyric acid (optionally substituted with a substituent selected from the group consisting of acyl, C$_1$-C$_4$ alkyl, aroyl, amidino, and MeC(NH)-), 2,3-diaminopropionic acid (optionally substituted with a substituent selected from the group consisting of acyl, C$_1$-C$_4$ alkyl, aroyl, amidino, and MeC(NH)-), glutamine, glycine, lysine (optionally substituted with a substituent selected from the group consisting of acyl, C$_1$-C$_4$ alkyl, aroyl, and MeC(NH)-), valine, methionine, serine (optionally substituted with a substituent selected from the group consisting of C$_1$-C$_4$ alkyl, aryl, and arC$_1$-C$_4$ alkyl), homoserine (optionally substituted with a substituent selected from the group consisting of C$_1$-C$_4$ alkyl, aryl, and arC$_1$-C$_4$ alkyl), threonine (optionally substituted with a substituent selected from the group consisting of C$_1$-C$_4$ alkyl, aryl, and arC$_1$-C$_4$ alkyl), ornithine (optionally substituted with a substituent selected from the group consisting of acyl, C$_1$-C$_4$ alkyl, aroyl, and MeC(NH)-), and an unsubstituted or substituted aromatic amino acid selected from the group consisting of phenylalanine, heteroarylalanine, and histidine, wherein the substituents on the aromatic amino acid are independently one to two substituents selected from the group consisting of halogen, C$_1$-C$_4$ alkyl, C$_1$-C$_4$ alkoxy, hydroxy, C$_1$-C$_4$ alkoxycarbonyl, amino, amidino, guanidino, fluorinated C$_1$-C$_4$ alkyl, fluorinated C$_1$-C$_4$ alkoxy, C$_1$-C$_4$ alkylsulfonyl, C$_1$-C$_4$ alkylcarbonyl, cyano, aryl, heteroaryl, arC$_1$-C$_4$ alkyl, C$_2$-C$_4$ alkenyl, alkynyl, and nitro;

R$_1$ is selected from the group consisting of diethylamino, di-(n-propyl)amino,

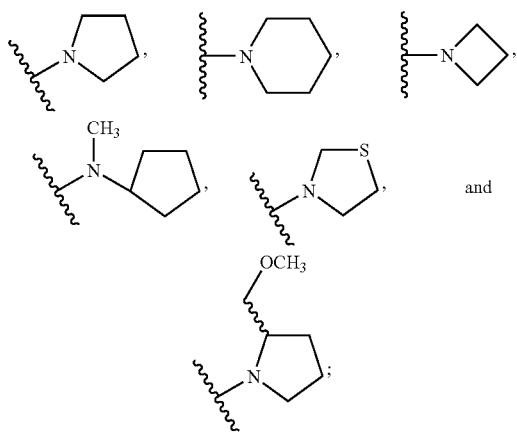

R$_2$ is selected from the group consisting of hydrogen, methyl and ethyl;

R$_3$ is selected from the group consisting of 2-indanyl, phenyl, cyclohexylmethyl, cyclopentyl, pyridylmethyl, furanylmethyl, 2-(4-methyl-furanyl)methyl, thienylmethyl, diphenylmethyl, 4-imidazolylethyl, 2-(4-N-methyl)imidazolylethyl, n-octyl, phenyl-n-propyl, aminoethyl, aminopropyl, amino-n-pentyl, dimethylaminoethyl, 4-aminophenylsulfonylaminomethyl, acetamidineylethyl, 2—N-pyrrolidinylethyl, N-ethoxycarbonylpiperidinyl, unsubstituted or substituted phenylethyl and unsubstituted or substituted benzyl wherein the substituents on the phenylethyl or benzyl are independently one or two substituents selected from the group consisting of methyl, fluorine, chlorine, nitro, methoxy, methoxycarbonyl and hydroxymethyl; or R$_2$ and R$_3$, together with the nitrogen to which they are attached, alternatively form a heteroalkyl group selected from the group consisting of piperidinyl, and $_4$-(N-methyl)piperazinyl; and R$_4$ is selected from the group consisting of cyclohexyl, 2-naphthyl, phenylethyl, 4-fluorophenylethyl and unsubstituted or substituted phenyl, where the substituents on the phenyl are independently selected from one to two substituents selected from the group consisting of fluorine, chlorine, iodine, methyl, cyano and trifluoromethyl; and pharmaceutically acceptable salts thereof.

7. The compound of claim 6, wherein:

R$_1$ is 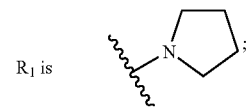

and pharmaceutically acceptable salts thereof.

8. The compound of claim 7, wherein:
R$_4$ is selected from the group consisting of

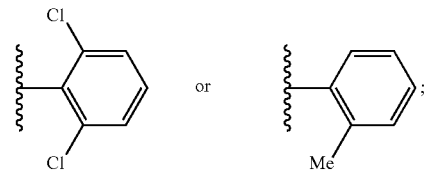

and pharmaceutically acceptable salts thereof.

9. The compound of claim 8, wherein:
A$_1$ is selected from the group consisting of 3,4-Difluorophenylalanine and 4-Chlorophenylalanine;
A$_2$ is selected from the group consisting of 2,4-Diaminobutyric acid and 4-Pyridylalanine;
R$_2$ is hydrogen; and
R$_3$ is selected from the group consisting of benzyl and 2-aminoethyl;
and pharmaceutically acceptable salts thereof.

10. A process for preparing a compound of the formula (II):

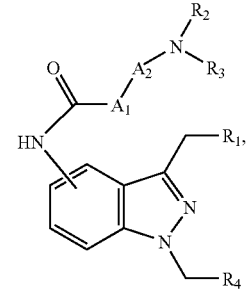

wherein:

A₁ and A₂ are each independently a D- or L-amino acid selected from the group consisting of alanine, β-alanine, arginine, homoarginine, cyclohexylalanine, citrulline, cysteine (optionally substituted with a substituent selected from the group consisting of $C_1$-$C_4$ alkyl, aryl, and ar$C_1$-$C_4$ alkyl), 2,4-diaminobutyric acid (optionally substituted with a substituent selected from the group consisting of acyl, $C_1$-$C_4$ alkyl, aroyl, amidino, and MeC(NH)-), 2,3-diaminopropionic acid (optionally substituted with a substituent selected from the group consisting of acyl, $C_1$-$C_4$ alkyl, aroyl, amidino, and MeC(NH)-), glutamine, glycine, indanylglycine, lysine (optionally substituted with a substituent selected from the group consisting of acyl, $C_1$-$C_4$ alkyl, aroyl, and MeC(NH)-), valine, methionine, proline, serine (optionally substituted with a substituent selected from the group consisting of $C_1$-$C_4$ alkyl, aryl, and ar$C_1$-$C_4$ alkyl), homoserine (optionally substituted with a substituent selected from the group consistingof$C_1$-$C_4$ alkyl, aryl, and ar$C_1$-$C_4$ alkyl), tetrahydroisoquinoline-3-COOH, threonine (optionally substituted with a substituent selected from the group consisting of $C_1$-$C_4$ alkyl, aryl, and ar$C_1$-$C_4$ alkyl), ornithine (optionally substituted with a substituent selected from the group consisting of acyl, $C_1$-$C_4$ alkyl, aroyl, and MeC(NH)-), and an unsubstituted or substituted aromatic amino acid selected from the group consisting of phenylalanine, heteroarylalanine, naphthylalanine, homophenylalanine, histidine, tryptophan, tyrosine, arylglycine, heteroaryiglycine, aryl-β-alanine, and heteroaryl-β-alanine wherein the substituents on the aromatic amino acid are independently selected from one or more the group consisting of halogen, $C_1$-$C_4$ alkyl, $C_1$-$C_4$ alkoxy, hydroxy, $C_1$-$C_4$ alkoxycarbonyl, amino, amidino, guanidino, fluorinated $C_1$-$C_4$ alkyl, fluorinated $C_1$-$C_4$ alkoxy, $C_1$-$C_4$ alkylsulfonyl, $C_1$-$C_4$ alkylcarbonyl, cyano, aryl, heteroaryl, ar$C_1$-$C_4$ alkyl, $C_2$-$C_4$ alkenyl, alkynyl, and nitro;

R₁ is selected from the group consisting amino, $C_1$-$C_8$ alkylamino, $C_1$-$C_8$ dialkylamino, arylamino, ar$C_1$-$C_8$ alkylamino, $C_3$-$C_8$ cycloalkylamino, heteroalkyl$C_1$-$C_8$ alkylamino, heteroalkyl$C_1$-$C_8$ alkyl-N-methylamino, $C_1$-$C_8$ dialkylamino$C_1$-$C_8$ alkylamino, —N($C_1$-$C_8$alkyl)-$C_1$-$C_8$ alkyl—N($C_1$-$C_8$alkyl)₂, N($C_1$-$C_8$alkyl) ($C_1$-$C_8$alkenyl), —N($C_1$-$C_8$alkyl)($C_3$-$C_8$cycloalkyl), heteroalkyl and substituted heteroalkyl wherein the substituent on the heteroalkyl is selected from the group consisting oxo, amino, $C_1$-$C_8$ alkoxy$C_1$-$C_8$ alkyl, $C_1$-$C_8$ alkylamino and $C_1$-$C_8$ dialkylamino;

R₂ and R₃ are each independently selected from the group consisting hydrogen, $C_1$-$C_8$ alkyl, $C_3$-$C_8$ cycloalkyl, $C_3$-$C_8$ cycloalkyl$C_1$-$C_8$ alkyl, aryl, heteroalkyl, substituted heteroalkyl (wherein the substituent on the heteroalkyl is one or more substituents independently selected from the group consisting $C_1$-$C_8$ alkoxycarbonyl, $C_1$-$C_8$ alkyl, and $C_1$-$C_4$ alkylcarbonyl), heteroalkyl$C_1$-$C_8$ alkyl, indanyl, acetamidino$C_1$-$C_8$ alkyl, amino$C_1$-$C_8$ alkyl, $C_1$-$C_8$ alkylamino$C_1$-$C_8$ alkyl, $C_1$-$C_8$ dialkylamino$C_1$-$C_8$ alkyl, unsubstituted or substituted heteroaryl$C_1$-$C_8$ alkyl and unsubstituted or substituted ar$C_1$-$C_8$ alkyl, wherein the substituent on the aralkyl or heteroarylalkyl group is one or more substituents independently selected from the group consisting halogen, nitro, amino, $C_1$-$C_8$ alkyl, $C_1$-$C_8$ alkoxy, hydroxy, cyano, $C_1$-$C_8$ alkylcarbonyl, $C_1$-$C_8$ alkoxycarbonyl, hydroxy$C_1$-$C_8$ alkyl and aminosulfonyl; or R₂ and R₃, together with the nitrogen to which they are attached, alternatively form an unsubstituted or substituted heteroalkyl group selected from the group consisting piperidinyl, piperazinyl, morpholinyl and pyrrolidinyl, wherein the substituent is one or more substituents independently selected from the group consisting $C_1$-$C_8$ alkyl $C_1$-$C_8$ alkoxycarbonyl and $C_1$-$C_4$ alkylcarbonyl;

R₄ is selected from the group consisting unsubstituted or substituted aryl, ar$C_1$-$C_8$ alkyl, $C_3$-$C_8$ cycloalkyl, and heteroaryl, where the substituents on the aryl, ar$C_1$-$C_8$ alkyl, cycloalkyl or heteroaryl group are independently selected from one or more the group consisting of halogen, nitro, amino, cyano, hydroxyalkyl, $C_1$-$C_8$ alkyl, $C_1$-$C_8$ alkoxy, hydroxy, $C_1$-$C_4$ alkylcarbonyl, $C_1$-$C_8$ alkoxycarbonyl, fluorinated $C_1$-$C_4$ alkyl, fluorinated $C_1$-$C_4$ alkoxy, and $C_1$-$C_4$ alkylsulfonyl;

comprising reacting a compound of the formula AAG6:
H-A₁-A₂-NR₂R₃, with a compound of the formula AAG4:

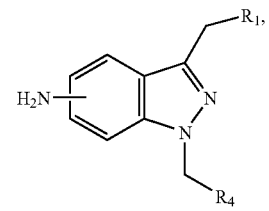

in the presence of a phosgene equivalent to form the compound of formula (II).

11. A method of treating a platelet-mediated thrombotic disorder selected from the group consisting of arterial thrombosis, venous thrombosis, acute myocardial infarction, reocciusion following thrombolytic therapy, reocclusion following angioplasty, unstable angina, and stroke in a subject in need thereof comprising administering to the subject a therapeutically effective amount of a compound of Formula (I):

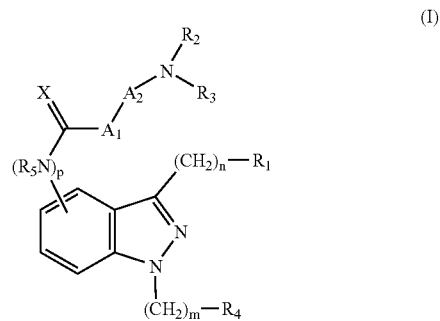

wherein:

A₁ and A₂ are each independently a D- or L-amino acid selected from the group consisting of alanine, β-alanine, arginine, homoarginine, cyclohexylalanine, citrulline, cysteine (optionally substituted with $C_1$-$C_4$ alkyl, aryl, or ar$C_1$-$C_4$ alkyl), 2,4-diaminobutyric acid (optionally substituted with acyl, $C_1$-$C_4$ alkyl, aroyl, amidino, or MeC(NH)-), 2,3-diaminopropionic acid (optionally substituted with acyl, $C_1$-$C_4$ alkyl, aroyl, amidino, or MeC(NH)-), glutamine, glycine, indanylglycine, lysine (optionally substituted with acyl, $C_1$-$C_4$ alkyl, aroyl, MeC(NH)-), valine, methionine, proline, serine (optionally substituted with $C_1$-$C_4$ alkyl, aryl, or ar$C_1$-$C_4$ alkyl), homoserine (optionally substituted with $C_1$-$C_4$ alkyl, aryl, or ar$C_1$-$C_4$ alkyl), tetrahydroisoquinoline-3-COOH, threonine (optionally substituted with $C_1$-$C_4$ alkyl, aryl, or ar$C_1$-$C_4$ alkyl), ornithine (optionally substituted with acyl, $C_1$-$C_4$ alkyl, aroyl, or MeC(NH)-), and an unsubstituted or substituted aromatic amino acid selected from the group consisting of phenylalanine, heteroarylalanine, naphthylalanine, homophenylalanine, histidine, tryptophan, tyrosine, arylglycine, heteroarylglycine, aryl-β-a₁anine, and heteroaryl-β-alanine wherein the substituents on the aromatic amino acid are independently selected from the group consisting of halogen, $C_1$-$C_4$ alkyl, $C_1$-$C_4$ alkoxy, hydroxy, $C_1$-$C_4$ alkoxycarbonyl, amino, amidino, guanidino, fluorinated $C_1$-$C_4$ alkyl, fluorinated $C_1$-$C_4$ alkoxy, $C_1$-$C_4$ alkylsulfonyl, $C_1$-$C_4$ alkylcarbonyl, cyano, aryl, heteroaryl, ar$C_1$-$C_4$ alkyl, $C_2$-$C_4$ alkenyl, alkynyl, and nitro;

$R_1$ is selected from the group consisting of amino, $C_1$-$C_8$ alkylamino, $C_1$-$C_8$ dialkylamino, arylamino, ar$C_1$-$C_8$ alkylamino, $C_3$-$C_8$ cycloalkylamino, heteroalkyl$C_1$-$C_8$ alkylamino, heteroalkyl$C_1$-$C_8$ alkyl-N-methylamino, $C_1$-$C_8$ dialkylamino$C_1$-$C_8$ alkylamino, —N($C_1$-$C_8$alkyl)-$C_1$-$C_8$ alkyl—N($C_1$-$C_8$alkyl)₂, N($C_1$-$C_8$alkyl)($C_1$-$C_8$alkenyl), —N($C_1$-$C_8$alkyl)($C_3$-$C_8$cycloalkyl), heteroalkyl and substituted heteroalkyl wherein the substituent on the heteroalkyl is selected from the group consisting of oxo, amino, $C_1$-$C_8$ alkoxy$C_1$-$C_8$ alkyl, $C_1$-$C_8$ alkylamino and $C_1$-$C_8$ dialkylamino;

$R_2$ and $R_3$ are each independently selected from the group consisting of hydrogen, $C_1$-$C_8$ alkyl, $C_3$-$C_8$ cycloalkyl, $C_3$-$C_8$ cycloalkyl$C_1$-$C_8$ alkyl, aryl, heteroalkyl, substituted heteroalkyl (wherein the substituent on the heteroalkyl is one or more substituents independently selected from the group consisting of $C_1$-$C_8$ alkoxycarbonyl, $C_1$-$C_8$ alkyl, and $C_1C_4$ alkylcarbonyl), heteroalkyl$C_1$-$C_8$ alkyl, indanyl, acetamidino$C_1$-$C_8$ alkyl, amino$C_1$-$C_8$ alkyl, $C_1$-$C_8$ alkylamino$C_1$-$C_8$ alkyl, $C_1$-$C_8$ dialkylamino$C_1$-$C_8$ alkyl, unsubstituted or substituted heteroaryl$C_1$-$C_8$ alkyl and or unsubstituted or substituted ar$C_1$-$C_8$ alkyl, wherein the substituent on the aralkyl or heteroarylalkyl group is one or more substituents independently selected from the group consisting of halogen, nitro, amino, $C_1$-$C_8$ alkyl, $C_1$-$C_8$ alkoxy, hydroxy, cyano, $C_1$-$C_4$ alkylcarbonyl, $C_1$-$C_8$ alkoxycarbonyl, hydroxy$C_1$-$C_8$ alkyl and aminosulfonyl; or $R_2$ and $R_3$, together with the nitrogen to which they are attached, alternatively form an unsubstituted or substituted heteroalkyl group selected from the group consisting of piperidinyl, piperazinyl, morpholinyl and pyrrolidinyl, wherein the substituent is one or more substituents independently selected from the group consisting of $C_1$-$C_8$ alkyl $C_1$-$C_8$ alkoxycarbonyl and $C_1$-$C_4$ alkylcarbonyl;

$R_4$ is selected from the group consisting of unsubstituted or substituted aryl, ar$C_1$-$C_8$ alkyl, $C_3$-$C_8$ cycloalkyl, and heteroaryl, where the substituents on the aryl, ar$C_1$-$C_8$ alkyl, cycloalkyl or heteroaryl group are independently selected from the group consisting of one or more of halogen, nitro, amino, cyano, hydroxyalkyl, $C_1$-$C_8$ alkyl, $C_1$-$C_8$ alkoxy, hydroxy, $C_1$-$C_4$ alkylcarbonyl, $C_1$-$C_8$ alkoxycarbonyl, fluorinated $C_1$-$C_4$ alkyl, fluorinated $C_1$-$C_4$ alkoxy, and $C_1$-$C_4$ alkylsulfonyl;

$R_5$ is selected from the group consisting of hydrogen and $C_1$-$C_8$ alkyl;

X is selected from the group consisting of oxygen and sulfur;

m is an integer selected from the group consisting of 0, 1, 2 and 3;

n is an integer selected from the group consisting of 1 and 2; and p is an integer selected from the group consisting of 0 and 1;

and pharmaceutically acceptable salts thereof.

12. The method of claim 11, wherein the therapeutically effective amount of the compound is from about 0.1 mg/kg/day to about 300 mg/kg/day.

13. The method of claim 11, wherein said compound is selected from the group consisting of:

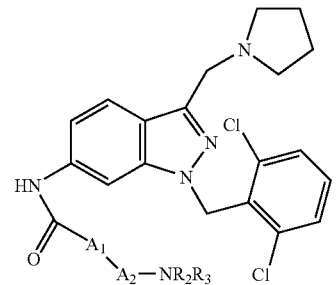

| Comp | $A_1$ | $A_2$ | $R_2R_3N$ |
|---|---|---|---|
| 1 | 3,4-DiF—Phe | Dbu | PhCH₂NH |
| 2 | 4-Cl—Phe | Dbu | PhCH₂NH |
| 3 | 3,4-DiF—Phe | 4-Pyrala | H₂NCH₂CH₂NH |
| 4 | 3,4-DiF—Phe | Dbu | R—PhCH(Me)NH |
| 5 | 3,4-DiF—Phe | Dbu | S—PhCH(CH₂OH)NH |
| 6 | 4-Cl—Phe | 2-Thiala | H₂NCH₂CH₂NH | wherein:
3,4-DiF-Phe is 3,4-diflourophenylalanine;
4-Cl-Phe is 4-chlorophenylalanine;
Dbu is 2,4-diaminobutyric acid;
4-Pyrala is 4-pyridylalanine; and
2-Thiala is 2-thienylalanine.

14. The method of claim 13, wherein said compound is Compound 1.

15. A method of treating restenosis in a subject in need thereof comprising administering to the subject a therapeutically effective amount of a compound of Formula (I):

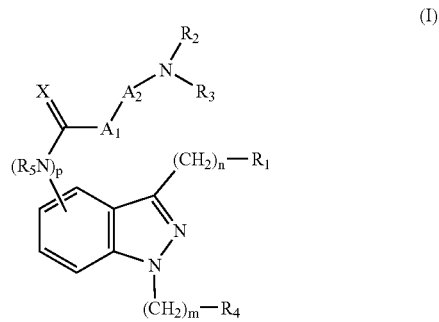

wherein:
$A_1$ and $A_2$ are each independently a D- or L-amino acid selected from the group consisting of alanine, β-alanine, arginine, homoarginine, cyclohexylalanine, citrulline, cysteine (optionally substituted with $C_1$-$C_4$ alkyl, aryl, or ar$C_1$-$C_4$ alkyl), 2,4-diaminobutyric acid (optionally substituted with acyl, $C_1$-$C_4$ alkyl, aroyl, amidino, or MeC(NH)-), 2,3-diaminopropionic acid (optionally substituted with acyl, $C_1$-$C_4$ alkyl, aroyl, amidino, or MeC(NH)-), glutamine, glycine, indanyiglycine, lysine (optionally substituted with acyl, $C_1$-$C_4$ alkyl, aroyl, MeC(NH)-), valine, methionine, proline, serine (optionally substituted with $C_1$-$C_4$ alkyl, aryl, or ar$C_1$-$C_4$ alkyl), homoserine (optionally substituted with $C_1$-$C_4$ alkyl, aryl, or ar$C_1$-$C_4$ alkyl), tetrahydroisoquinoline-3-COOH, threonine (optionally substituted with $C_1$-$C_4$ alkyl, aryl, or ar$C_1$-$C_4$ alkyl), ornithine (optionally substituted with acyl, $C_1$-$C_4$ alkyl, aroyl, or MeC(NH)-), and an unsubstituted or substituted aromatic amino acid selected from the group consisting of phenylalanine, heteroarylalanine, naphthylalanine, homophenylalanine, histidine, tryptophan, tyrosine, arylglycine, heteroarylglycine, aryl-β-alanine, and heteroaryl-β-alanine wherein the substituents on the aromatic amino acid are independently selected from the group consisting of halogen, $C_1$-$C_4$ alkyl, $C_1$-$C_4$ alkoxy, hydroxy, $C_1$-$C_4$ alkoxycarbonyl, amino, amidino, guanidino, fluorinated $C_1$-$C_4$ alkyl, fluorinated $C_1$-$C_4$ alkoxy, $C_1$-$C_4$ alkylsulfonyl, $C_1$-$C_4$ alkylcarbonyl, cyano, aryl, heteroaryl, ar$C_1$-$C_4$ alkyl, $C_2$-$C_4$ alkenyl, alkynyl, and-nitro;

$R_1$ is selected from the group consisting of amino, $C_1$-$C_8$ alkylamino, $C_1$-$C_8$ dialkylamino, arylamino, ar$C_1$-$C_8$ alkylamino, $C_3$-$C_8$ cycloalkylamino, heteroalkyl$C_1$-$C_8$ alkylamino, heteroalkyl$C_1$-$C_8$ alkyl-N-methylamino, $C_1$-$C_8$ dialkylamino$C_1$-$C_8$ alkylamino, —N($C_1$-$C_8$alkyl)-$C_1$-$C_8$ alkyl—N($C_1$-$C_8$alkyl)$_2$, N($C_1$-$C_8$alkyl)($C_1$-$C_8$alkenyl), —N($C_1$-$C_8$alkyl)($C_3$-$C_8$cycloalkyl), heteroalkyl and substituted heteroalkyl wherein the substituent on the heteroalkyl is selected from the group consisting of oxo, amino, $C_1$-$C_8$ alkoxy$C_1$-$C_8$ alkyl, $C_1$-$C_8$ alkylamino and $C_1$-$C_8$ dialkylamino;

$R_2$ and $R_3$ are each independently selected from the group consisting of hydrogen, $C_1$-$C_8$ alkyl, $C_3$-$C_8$ cycloalkyl, $C_3$-$C_8$ cycloalkyl$C_1$-$C_8$ alkyl, aryl, heteroalkyl, substituted heteroalkyl (wherein the substituent on the heteroalkyl is one or more substituents independently selected from the group consisting of $C_1$-$C_8$ alkoxycarbonyl, $C_1$-$C_8$ alkyl, and $C_1C_4$ alkylcarbonyl), heteroalkyl$C_1$-$C_8$ alkyl, indanyl, acetamidino$C_1$-$C_8$ alkyl, amino$C_1$-$C_8$ alkyl, $C_1$-$C_8$ alkylamino$C_1$-$C_8$ alkyl, $C_1$-$C_8$ dialkylamino$C_1$-$C_8$ alkyl, unsubstituted or substituted heteroaryl$C_1$-$C_8$ alkyl and or unsubstituted or substituted ar$C_1$-$C_8$ alkyl, wherein the substituent on the aralkyl or heteroarylalkyl group is one or more substituents independently selected from the group consisting of halogen, nitro, amino, $C_1$-$C_8$ alkyl, $C_1$-$C_8$ alkoxy, hydroxy, cyano, $C_1$-$C_4$ alkylcarbonyl, $C_1$-$C_8$ alkoxycarbonyl, hydroxy$C_1$-$C_8$ alkyl and aminosulfonyl; or $R_2$ and $R_3$, together with the nitrogen to which they are attached, alternatively form an unsubstituted or substituted heteroalkyl group selected from the group consisting of piperidinyl, piperazinyl, morpholinyl and pyrrolidinyl, wherein the substituent is one or more substituents independently selected from the group consisting of $C_1$-$C_8$ alkyl $C_1$-$C_8$ alkoxycarbonyl and $C_1$-$C_4$ alkylcarbonyl;

$R_4$ is selected from the group consisting of unsubstituted or substituted aryl, ar$C_1$-$C_8$ alkyl, $C_3$-$C_8$ cycloalkyl, and heteroaryl, where the substituents on the aryl, ar$C_1$-$C_8$ alkyl, cycloalkyl or heteroaryl group are independently selected from the group consisting of one or more of halogen, nitro, amino, cyano, hydroxyalkyl, $C_1$-$C_8$ alkyl, $C_1$-$C_8$ alkoxy, hydroxy, $C_1$-$C_4$ alkylcarbonyl, $C_1$-$C_8$ alkoxycarbonyl, fluorinated $C_1$-$C_4$ alkyl, fluorinated $C_1$-$C_4$ alkoxy, and $C_1$-$C_4$ alkylsulfonyl;

$R_5$ is selected from the group consisting of hydrogen and $C_1$-$C_8$ alkyl;

X is selected from the group consisting of oxygen and sulfur;

m is an integer selected from the group consisting of 0, 1, 2 and 3;

n is an integer selected from the group consisting of 1 and 2; and p is an integer selected from the group consisting of 0 and 1;

and pharmaceutically acceptable salts thereof.

16. The method of claim 15, wherein the therapeutically effective amount of the compound is from about 0.1 mg/kg/day to about 300 mg/kg/day.

17. The method of claim 15, wherein said compound is selected from the group consisting of:

| Comp | $A_1$ | $A_2$ | $R_2R_3N$ |
|------|-------|-------|-----------|
| 1 | 3,4-DiF—Phe | Dbu | PhCH$_2$NH |
| 2 | 4-Cl—Phe | Dbu | PhCH$_2$NH |
| 3 | 3,4-DiF—Phe | 4-Pyrala | H$_2$NCH$_2$CH$_2$NH |
| 4 | 3,4-DiF—Phe | Dbu | R—PhCH(Me)NH |
| 5 | 3,4-DiF—Phe | Dbu | S—PhCH(CH$_2$OH)NH |
| 6 | 4-Cl—Phe | 2-Thiala | H$_2$NCH$_2$CH$_2$NH | wherein:
  3,4-DiF-Phe is 3,4-diflourophenylanine;
  4-Cl-Phe is 4-chlorophenylanine;
  Dbu is 2,4-diaminobutyric acid;
  4-Pyrala is 4-pyridylalanine; and
  2-Thalia is 2thienylalnine.

18. The method of claim 17, wherein said compound is Compound 1.

* * * * *